(12) United States Patent
Surine et al.

(10) Patent No.: US 11,801,341 B2
(45) Date of Patent: Oct. 31, 2023

(54) USER EXPERIENCE FOR INFUSION PUMPS

(71) Applicant: Smiths Medical ASD, Inc., Plymouth, MN (US)

(72) Inventors: James Surine, Oakdale, MN (US); Grant A. Adams, Anoka, MN (US); Ryan D. Heilman, Andover, MN (US); Ricky Ledford, Brooklyn Park, MN (US); Nancy Bayer, Arden Hills, MN (US); Gail B. Bynum, Brooklyn Park, MN (US); James B. Drost, Maple Grove, MN (US); Chris Pickles, Bridport (GB); Lisa Hoh, St. Paul, MN (US); Jennifer Tsai, Stillwater, MN (US); Eric J. Wilkowske, North Oaks, MN (US); Nathan Vang, St. Paul, MN (US); Kou Lor, St. Paul, MN (US); Janet Shallbetter, Brooklyn Park, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 660 days.

(21) Appl. No.: 16/642,127

(22) PCT Filed: Sep. 12, 2018

(86) PCT No.: PCT/US2018/050664
§ 371 (c)(1),
(2) Date: Feb. 26, 2020

(87) PCT Pub. No.: WO2019/055516
PCT Pub. Date: Mar. 21, 2019

(65) Prior Publication Data
US 2021/0162115 A1    Jun. 3, 2021

Related U.S. Application Data

(60) Provisional application No. 62/557,243, filed on Sep. 12, 2017.

(51) Int. Cl.
*A61M 5/142* (2006.01)
*G06F 3/0484* (2022.01)
(Continued)

(52) U.S. Cl.
CPC ............ *A61M 5/142* (2013.01); *A61M 5/168* (2013.01); *G06F 3/0484* (2013.01);
(Continued)

(58) Field of Classification Search
None
See application file for complete search history.

(56) References Cited

U.S. PATENT DOCUMENTS

| 4,756,706 A | 7/1988 | Kerns et al. |
| 4,898,578 A | 2/1990 | Rubalcaba, Jr. |

(Continued)

FOREIGN PATENT DOCUMENTS

| WO | WO-2015047595 A1 | 4/2015 |
| WO | WO-2016036554 A1 | 3/2016 |
| WO | WO-2016118330 A1 | 7/2016 |

OTHER PUBLICATIONS

International Preliminary Report on Patentability from PCT Application PCT/US2018/050664, dated Mar. 26, 2020, 9 pgs.

(Continued)

*Primary Examiner* — Jenna Zhang
(74) *Attorney, Agent, or Firm* — Patterson Thuente IP

(57) ABSTRACT

Infusion pump interfaces providing simple and intuitive user experiences. A controller display subsystem for implementing infusion pump interfaces includes a processor, a memory, display logic, keypad I/O, and screen I/O. Display logic can command the processor via the memory to implement desirable displays on screen I/O.

8 Claims, 18 Drawing Sheets

(51) Int. Cl.
*A61M 5/168* (2006.01)
*G06F 3/0488* (2022.01)

(52) U.S. Cl.
CPC . *G06F 3/0488* (2013.01); *A61M 2005/14208* (2013.01); *A61M 2205/18* (2013.01); *A61M 2205/3327* (2013.01); *A61M 2205/3334* (2013.01); *A61M 2205/35* (2013.01); *A61M 2205/505* (2013.01); *A61M 2205/584* (2013.01); *A61M 2205/8206* (2013.01)

(56) References Cited

U.S. PATENT DOCUMENTS

| | | | |
|---|---|---|---|
| 5,782,805 A | 7/1998 | Meinzer et al. | |
| 6,775,577 B2 | 8/2004 | Crnkovich et al. | |
| 6,790,198 B1 | 9/2004 | White et al. | |
| 7,398,183 B2 | 7/2008 | Holland et al. | |
| 7,454,314 B2 | 11/2008 | Holland et al. | |
| 7,490,021 B2 | 2/2009 | Holland et al. | |
| 7,645,258 B2 | 1/2010 | White et al. | |
| 7,895,053 B2 | 2/2011 | Holland et al. | |
| 7,896,842 B2 | 3/2011 | Palmroos et al. | |
| 7,945,452 B2 | 5/2011 | Fathallah et al. | |
| 8,065,161 B2 | 11/2011 | Howard et al. | |
| 8,078,983 B2 | 12/2011 | Davis et al. | |
| 8,185,322 B2 | 5/2012 | Schroeder et al. | |
| 8,209,060 B2 | 6/2012 | Ledford | |
| 8,250,483 B2 | 8/2012 | Blomquist | |
| 8,317,752 B2 | 11/2012 | Cozmi et al. | |
| 8,486,019 B2 | 7/2013 | White et al. | |
| 8,494,879 B2 | 7/2013 | Davis et al. | |
| 8,517,990 B2 | 8/2013 | Teel, IV et al. | |
| 8,518,021 B2 | 8/2013 | Stewart et al. | |
| 8,543,416 B2 | 9/2013 | Palmroos et al. | |
| 8,552,880 B2 | 10/2013 | Kopp et al. | |
| 8,560,345 B2 | 10/2013 | Wehba et al. | |
| 8,577,692 B2 | 11/2013 | Silkaitis et al. | |
| 8,655,676 B2 | 2/2014 | Wehba et al. | |
| 8,700,421 B2 | 4/2014 | Feng et al. | |
| 8,768,717 B2 | 7/2014 | Blomquist | |
| 8,768,719 B2 | 7/2014 | Wehba et al. | |
| 8,858,526 B2 | 10/2014 | Blomquist | |
| 8,974,406 B2 | 3/2015 | Evans et al. | |
| 9,026,370 B2 | 5/2015 | Rubalcaba, Jr. et al. | |
| 9,240,002 B2 | 1/2016 | Hume et al. | |
| 9,381,296 B2 | 7/2016 | Arrizza et al. | |
| 9,393,362 B2 | 7/2016 | Cozmi et al. | |
| 9,662,436 B2 | 5/2017 | Belkin et al. | |
| D812,218 S | 3/2018 | Lacy et al. | |
| D816,696 S | 5/2018 | Ledford et al. | |
| D816,697 S | 5/2018 | Ledford et al. | |
| D816,699 S | 5/2018 | Ledford et al. | |
| D816,700 S | 5/2018 | Bayer et al. | |
| D823,456 S | 7/2018 | Lacy et al. | |
| D828,366 S | 9/2018 | Bayer et al. | |
| D828,547 S | 9/2018 | Lacy et al. | |
| 10,155,084 B2 | 12/2018 | Blomquist | |
| 10,255,408 B2 | 4/2019 | Blomquist | |
| D868,111 S | 11/2019 | Ledford et al. | |
| D868,837 S | 12/2019 | Bayer et al. | |
| 10,635,784 B2 | 4/2020 | Rubalcaba, Jr. et al. | |
| 2004/0243977 A1* | 12/2004 | Shou | G06F 8/33 717/112 |
| 2005/0177111 A1 | 8/2005 | Ozeri et al. | |
| 2006/0229557 A1 | 10/2006 | Fathallah et al. | |
| 2008/0033360 A1 | 2/2008 | Evans et al. | |
| 2008/0126969 A1 | 5/2008 | Blomquist | |
| 2008/0200870 A1 | 8/2008 | Palmroos et al. | |
| 2009/0153058 A1 | 6/2009 | Feng et al. | |
| 2009/0153463 A1 | 6/2009 | Arrizza et al. | |
| 2009/0153595 A1 | 6/2009 | Cozmi et al. | |
| 2009/0157432 A1 | 6/2009 | Palmroos et al. | |
| 2009/0171289 A1 | 7/2009 | Davis et al. | |
| 2009/0177180 A1 | 7/2009 | Rubalcaba, Jr. et al. | |
| 2009/0177991 A1 | 7/2009 | Davis et al. | |
| 2009/0177992 A1 | 7/2009 | Rubalcaba, Jr. et al. | |
| 2009/0183105 A1 | 7/2009 | Teel, IV et al. | |
| 2009/0183147 A1 | 7/2009 | Davis et al. | |
| 2010/0010647 A1 | 1/2010 | Schroeder et al. | |
| 2010/0100037 A1 | 4/2010 | Cozmi et al. | |
| 2010/0293496 A1 | 11/2010 | Lafferty et al. | |
| 2012/0130308 A1 | 5/2012 | Silkaitis et al. | |
| 2012/0306881 A1* | 12/2012 | Nemoto | G16H 40/63 345/440 |
| 2013/0332874 A1 | 12/2013 | Rosinko et al. | |
| 2016/0228633 A1 | 8/2016 | Welsch et al. | |
| 2016/0256622 A1* | 9/2016 | Day | A61M 5/1407 |
| 2016/0271325 A1 | 9/2016 | Farnan et al. | |
| 2017/0213012 A1 | 7/2017 | O'Scolai et al. | |
| 2020/0118664 A1 | 4/2020 | Blomquist | |

OTHER PUBLICATIONS

PCT International Search Report and Written Opinion for International Application No. PC/US2018/050664 dated Mar. 20, 2019, 11 pages.

Gorges Matthias: "Signal processing, human factors, and modelling to support bedside care in the intensive care in the intensive care unit", i Jan. 2012 (Jan. 1, 2012), XP055801233, DOI: 10.26053/Oh-vrmv-3r00 Retrieved from the Internet: URL:https://collections.lib.utah.edu/dl_files/dd/95/dd959a613ec16680924b9a672e1b5d56faef4944.pdf [retrieved on May 4, 2021] * the whole document *.

Supplemental Partial European Search Report from Application EP 18855742, dated May 4, 2021, 13 pgs.

Extended European Search Report from Application EP 18855742, dated Aug. 8, 2021, 11 pgs.

* cited by examiner

NICU

Select Drug Protocol:Antibiotics

Cefotetan 40mg/mL
CefoXITIN 40mg/mL
CefTAZidime 100mg/mL
Clindamycin 10mg/mL

Page: | 1 | 2 | 3 |

FIG. 19

NICU

Ampicillin 100 mg/mL

Dose: 275.00 mg/kg
Concentration: 100.00 mg/mL
Weight: 68.00 kg
Rate: mL/h
Infusion Duration: hh:mm:ss Confirm | More ▲ | Delivery Options

| 1 | 2 | 3 |
| 4 | 5 | 6 |
| 7 | 8 | 9 |
| ⌫ | 0 | . |

USER EXPERIENCE FOR INFUSION PUMPS

CROSS-REFERENCE TO RELATED APPLICATION

The present application claims priority to U.S. Provisional Application No. 62/557,243, filed on Sep. 12, 2017, which is hereby fully incorporated herein by reference.

TECHNICAL FIELD

Embodiments relate generally to medical devices and, more particularly, to user experience for infusion pumps including syringe pumps and large volume pumps (LVPs).

BACKGROUND

In the medical arts, infusion pumps have been useful for managing the delivery and dispensation of a prescribed amount or dose of a drug, fluid, fluid-like substance, or medicament (hereinafter, collectively, an "infusate" or "infusates") to patients. Infusion pumps can provide some significant advantages over manual infusion techniques, by accurately delivering and dispensing infusates over an extended period of time.

Infusion pumps are particularly useful for treating diseases and disorders that require regular pharmacological intervention, including cancer, diabetes, and vascular, neurological, and metabolic disorders. They also enhance the ability of healthcare providers to deliver anesthesia and manage pain. Infusion pumps are used in various settings, including hospitals, nursing homes, and other short-term and long-term medical facilities, as well as in residential care settings. Infusion pumps can include various constructions, modes of operation, and types.

Generally, infusion pumps can comprise a variety of types of pumps. In some cases, infusion pumps include syringe pumps and LVPs. Depending upon their specific designs and intended uses, infusion pumps can be used to administer infusates through various delivery methods, including intravenously, intraperitoneally, intra-arterially, subcutaneously, neuraxially, and specifically into an intraoperative site, epidural space, and subarachnoid space.

While various syringe pumps and LVPs have been used for many years, these devices can at times be difficult, inefficient, or cumbersome to use. In particular, infusion pump user interfaces often require multiple tedious inputs by a user. Also, infusion pumps can have difficult to use or confusing workflows, and can be generally inflexible in the order of data that can be entered. Therefore, there is a need for infusion pumps that tend to not be difficult, inefficient, or cumbersome to use; and there is also a need for improved infusion pump interfaces that provide simple and intuitive experiences for the user including more usable, flexible workflows.

SUMMARY

Embodiments described herein substantially meet the aforementioned needs of the industry. Infusion pump interfaces described herein provide simple and intuitive experiences for the user including usable, flexible workflows.

In an embodiment of a system for controlling an infusion pump display, the infusion pump includes a processor, memory operably coupled to the processor, and display logic comprising instructions that, when executed, cause the processor to display a first subset of infusion parameters on a first running screen; and display a second subset of infusion parameters on a second running screen, wherein the first subset of infusion parameters is greater than the second subset of infusion parameters and the display of the first subset of infusion parameters is in a smaller presentation size than the display of the second subset of infusion parameters.

In an embodiment of a system for controlling an infusion pump display, the infusion pump includes a processor, memory operably coupled to the processor, and display logic comprising instructions that, when executed, cause the processor to display a first subset of infusion parameters on a first running screen of the infusion pump; display a second subset of infusion parameters on a second running screen of the infusion pump, wherein the first subset of infusion parameters is greater than the second subset of infusion parameters and the display of the first subset of infusion parameters is in a smaller presentation size than the display of the second subset of infusion parameters; evaluate a condition related to the infusion pump; and based on the evaluation of the condition, automatically and without user intervention, display a specialized screen related to a current status of the system.

In an embodiment, a method for programming an infusion pump comprises providing an infusion pump including a processor, memory operably coupled to the processor, and display logic configured to present an infusion pump touchscreen interface and a tactile infusion pump interface; receiving at least one infusion pump programming input on the infusion pump touchscreen interface; receiving an infusion pump initiation command on the tactile infusion pump interface; and locking the infusion pump touchscreen interface upon beginning the infusion in response to the infusion pump initiation command.

In an embodiment, a method for programming an infusion pump comprises providing an infusion pump including a processor, memory operably coupled to the processor, an infusion pump touchscreen interface, and a tactile infusion pump interface, wherein the processor is configured to display infusion pump data using the infusion pump touchscreen interface and receive infusion pump data from the infusion pump touchscreen interface and the tactile infusion pump interface; receiving at least one infusion pump programming input on the infusion pump touchscreen interface; receiving an infusion pump initiation command on the tactile infusion pump interface; and locking the infusion pump touchscreen interface upon beginning the infusion in response to the infusion pump initiation command.

In an embodiment, a method for programming a syringe pump, the syringe pump including a processor, memory operably coupled to the processor, and display logic configured to present a touchscreen interface, comprises receiving a syringe in a syringe loading area of the syringe pump; presenting, by the display logic, a programming interface in which infusion parameters related to the syringe can be entered in any order; and starting an infusion with the syringe using the infusion parameters.

In an embodiment, a method for programming a syringe pump, the syringe pump including a processor, memory operably coupled to the processor, and display logic configured to present a touchscreen interface, the method comprises receiving a syringe in a syringe loading area of the syringe pump; presenting, by the display logic, a programming interface in which infusion parameters related to the syringe can be entered in any order; and starting an infusion with the syringe using the infusion parameters.

In a feature and advantage of embodiments, infusion pumps implementing the systems and methods described herein provide flexibility in setup. In embodiments, less interface touching is required compared to other infusion pumps. For example, traditional infusion pumps typically require a user programming the pumps to step through a fixed process of inputting parameters for an infusion. However, embodiments described by example or otherwise contemplated herein provide flexibility in parameter inputting, including by displaying all editable parameters on the screen at a same time or nearly so such that parameters can be edited in any order. Further, for syringe pumps, embodiments allow parameters to be set prior to or after the syringe is loaded.

In another feature and advantage, the interfaces described herein provide for enhanced safety. For example, a problem can occur where multiple touches are allowed, and liquid droplets contacting the screen trigger inadvertent "touches." Embodiments are therefore designed to respond only to a single touch and release. Further, the user interface can be configured to ignore any swiping or double-touching.

In another feature and advantage of embodiments, touch points on the infusion pump are color-coded for intuitive recognition by the user. For example, areas of the interface available for a medical practitioner to edit or modify can be colored blue, while areas of the interface that are fixed or cannot be edited can be colored gray. Thus, a busy user (throughout this document, "user" is intended to include an authorized operator of a pump such as, for example, a clinician or nurse, or even a patient) can easily determine the sections for which he is responsible and "ignore" or move quickly over sections that are fixed. This color-coding can be consistent between the graphical user interface on a touch-screen and mechanical components on the infusion pump that also require adjustment or user input (for example, the syringe loading area of a syringe pump).

In another feature and advantage of embodiments, touch lock algorithms protect the touchscreen display from inadvertent touches. For example, when an infusion starts, the touchscreen display is viewable but is immediately locked. In other embodiments, the user can lock the screen any time by tapping a lock icon in on the display. When the screen is locked the display is still visible and does not have a disabled appearance. However, when locked, the only area of the screen that accepts touch input is the touch target for the lock/unlock icon.

In another feature and advantage of embodiments, infusion pump displays provide visually helpful near-run screens and far-run screens. Near-run screens are configured to be read by users relatively close to the infusion pump display. Near-run screens are therefore configured to display relatively more information in a smaller size than far-run screens. In an embodiment, a top four-to-six items of information for the infusion or infusion pump can be displayed. In another embodiment, additional information can be presented to the user.

Far-run screens are configured to be read by users relatively far from the infusion pump display. Far-run screens are therefore configured to display relatively less information in a larger size than near-run screens. In one embodiment, top two items of information for the infusion or infusion pump can be displayed (such as dose and rate). In another embodiment, a relatively small number of parameters can be displayed in a large size, with additional parameters also displayed but in a comparatively smaller size and not intended to be viewed by the user from a distance.

Accordingly, display logic of the infusion pump is configured to intelligently display infusion parameters to the user using near-run screens and far-run screens. In an embodiment, a near-run screen can comprise a first subset of the infusion parameters displayed or presented to the user using a relatively small size font or graphical display. A far-run screen can comprise a second subset of the infusion parameters displayed or presented to the user at a relatively larger size font or graphical display, wherein the second subset is less than the first subset. In embodiments, the second subset comprises a selected one or more of the infusion parameters from the first subset. Thus, a user is able to view several or all of the infusion parameters on a near-run screen (due to the smaller font or presentation size), and relatively fewer infusion parameters on a far-run screen (due to the larger font or presentation size). Important or critical infusion parameters can be presented on the far-run screen in the larger size.

Algorithms intelligently control near-run screens and far-run screens. For example, an infusion can be started and the infusion pump can be configured to display the infusion parameters in a near-run screen. After a selected time has elapsed (or other suitable trigger point), the infusion pump can be configured to display the relevant parameters in a far-run screen. This workflow mirrors the typical medical professional workflow in which the user has programmed the pump, departed from a vicinity near the pump, and desires to check on the pump or patient a short time later at a distance after the infusion has been running. The algorithms implemented herein in combination with near-run/far-run screens further solve the problem that exists with traditional infusion pumps when nurses place tape on the infusion pump with writing larger than the typical (small) display that has the information they need to be able to see at a distance.

In another feature and advantage of embodiments, alarms are provided with guided help to assist the user. For example, an alarm related to the infusion or infusion pump can be presented to the user, along with an information icon. The information icon can be selected (or in combination with larger touch target areas), which causes the infusion pump to present additional details about the alarm and, if applicable, instructions for correcting the condition that triggered the alarm.

In another feature and advantage of embodiments, a flexible three-way drug lookup is provided. For example, a display screen can present an "alphanumeric A-Z" lookup, a free text "Search" lookup, and a "Category" lookup for various drug protocol options. These lookups allow a programming user flexibility to quickly find the desired drug protocol, depending on the user's preference and/or the drug protocol being searched.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

Figures 13B, 13C:
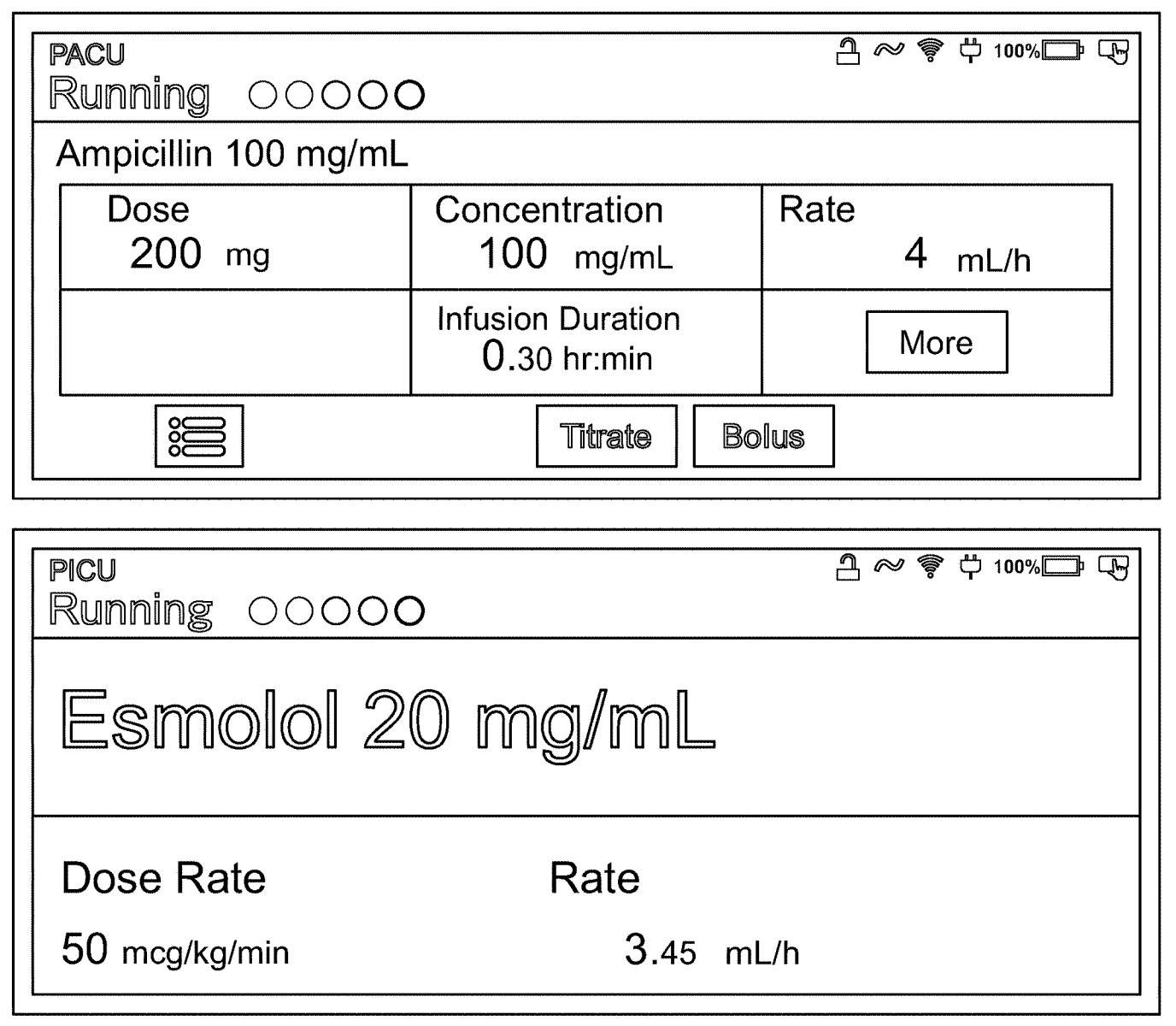

FIG. 13A is a screenshot of a ready-to-run screen for an infusion pump touchscreen display, according to an embodiment.

FIG. 13B is a screenshot of a near-run screen for an infusion pump touchscreen display, according to an embodiment.

FIG. 13C is a screenshot of a far-run screen for an infusion pump touchscreen display, according to an embodiment.

FIG. 18 is a screenshot of a drug protocol categories lookup screen for an infusion pump touchscreen display, according to an embodiment.

FIG. 19 is a screenshot of a program parameters screen for an infusion pump touchscreen display, according to an embodiment.

Figure 1:
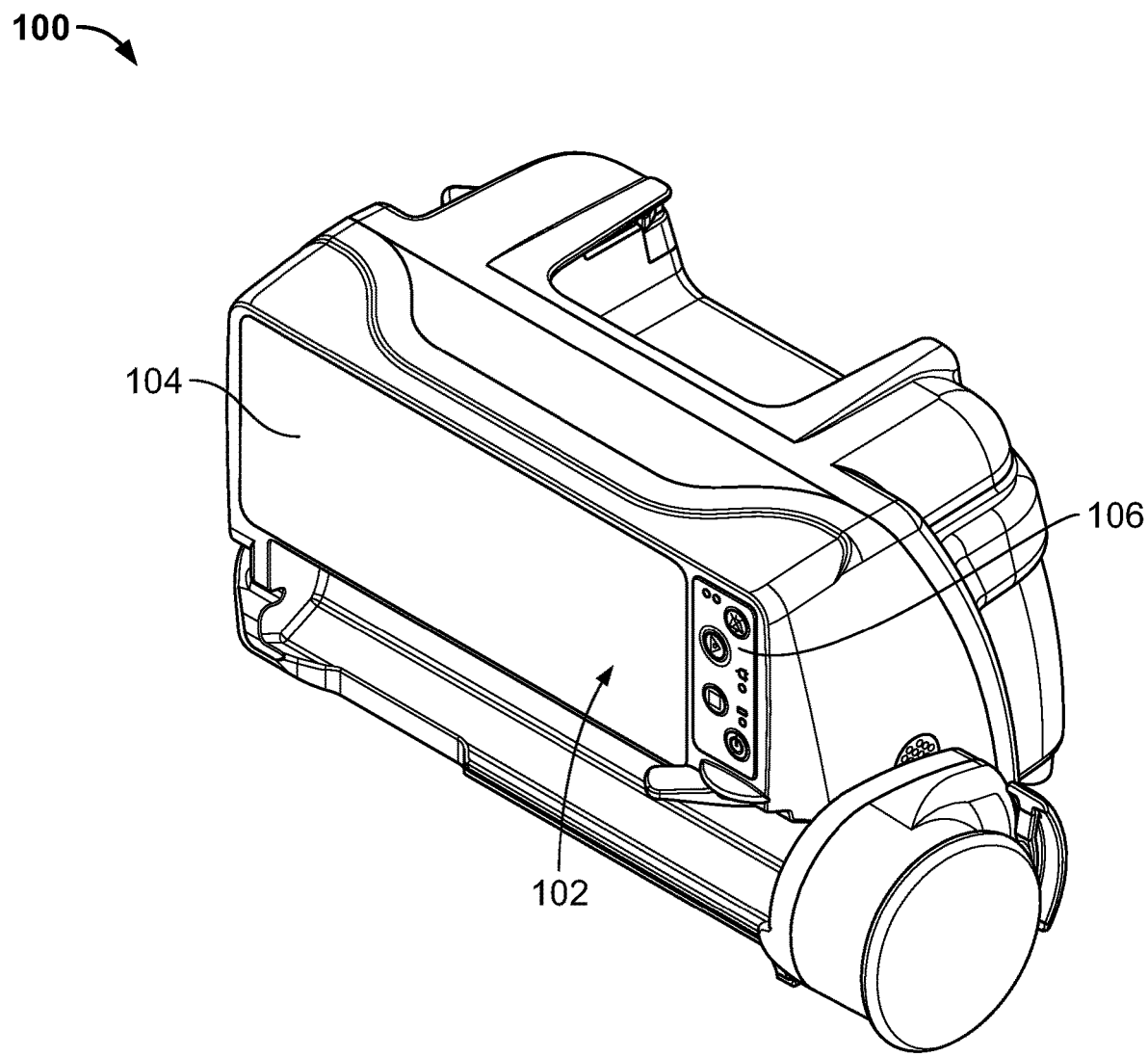
FIG. 1 is a front corner perspective view of an infusion pump comprising a syringe pump, according to an embodiment.

While various embodiments are amenable to various modifications and alternative forms, specifics thereof have been shown by way of example in the drawings and will be described in detail. It should be understood, however, that the intention is not to limit the claimed subject matter to the particular embodiments described. On the contrary, the intention is to cover all modifications, equivalents, and alternatives falling within the spirit and scope of the subject matter as defined by the claims.

DETAILED DESCRIPTION OF THE DRAWINGS

Figure 2:
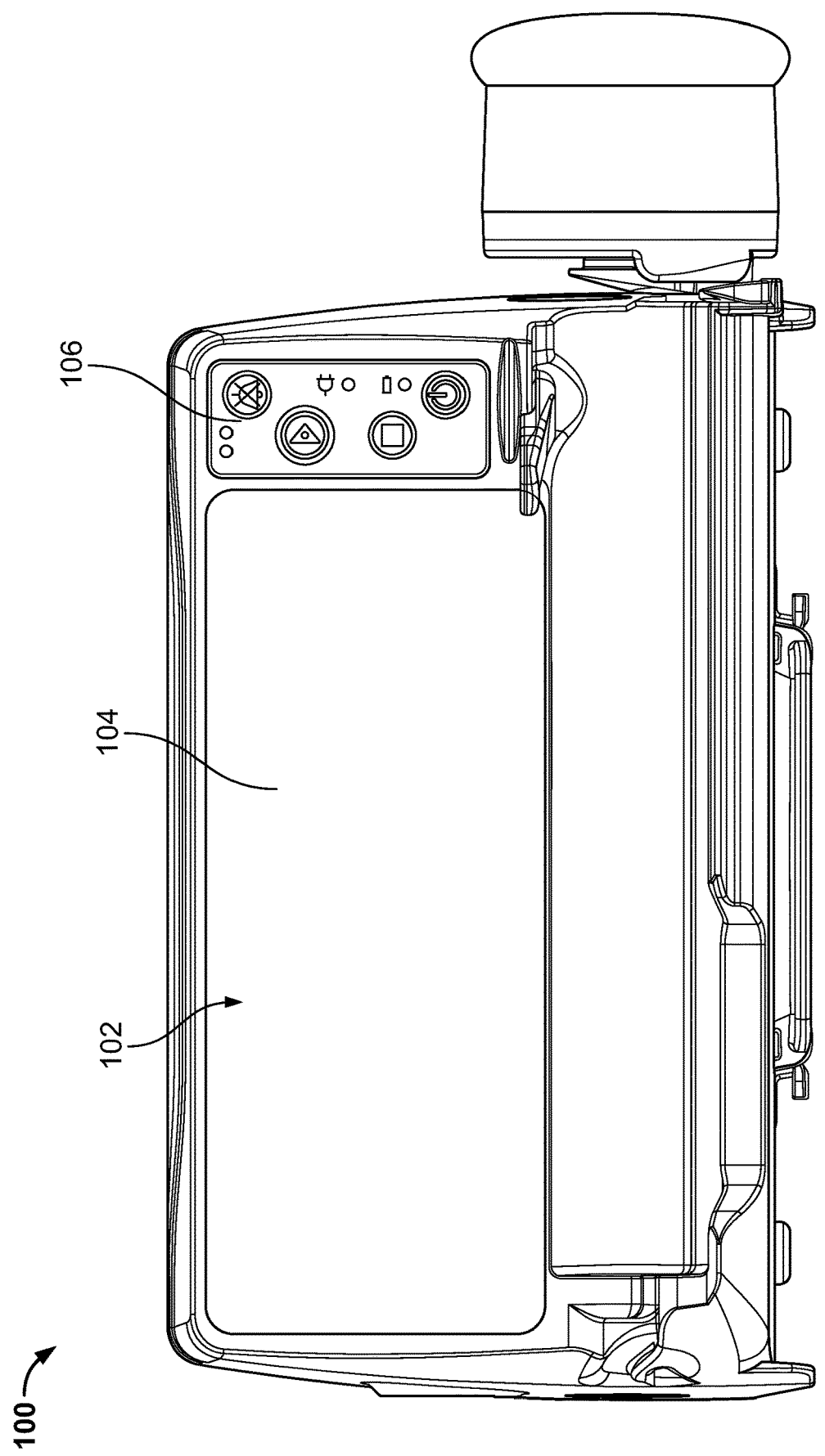
FIG. 2 is a front view of an infusion pump comprising a syringe pump, according to an embodiment.

Referring to FIGS. 1-2, an infusion pump, and particularly, a syringe pump 100 is shown. One skilled in the art will readily appreciate that the user experience embodiments described herein can be configured to be utilized with syringe pumps, large volume pumps, and patient-controlled analgesia ("PCA") pumps.

"Syringe pumps" generally include pumps for acting on a pre-filled medication syringe that is mechanically driven under microprocessor control to deliver a prescribed amount or dose of a fluid at a controlled rate to a patient through an infusion line fluidly connected to the syringe. Syringe pumps typically include a motor that rotates a leadscrew or adjustment mechanism, for example. The leadscrew or adjustment mechanism, in turn, activates a plunger driver of the plunger head which forwardly pushes a plunger within a barrel of the syringe. Pushing the plunger forward then forces the dose of medication outwardly from the syringe, into the infusion line, and to the patient. As used throughout this disclosure, the term "syringe pump" is intended to generally pertain to any device which acts on a syringe to controllably force fluid outwardly therefrom.

"LVPs" can take on various forms, but are typically infusion pumps coupled to one or more reservoirs configured to hold or store a large amount of medication or fluid to be infused, such as a cassette, IV bag, or other self-contained fluid source. As used throughout this disclosure, the term "LVP" is intended to generally pertain to any infusion pump or device capable of large volume infusion to a patient.

Pump 100 generally comprises a user interface 102. User interface 102 generally includes a display screen 104 and a keypad 106.

Display screen 104 can be a rectangular, color, LCD screen, and can be a touchscreen in certain embodiments. Display screen 104 can be any type of graphical user interface ("GUI") for use in controlling pump 100. In some embodiments, display screen 104 can be configured to permit display of four lines of text, up to thirty characters long each. Accordingly, this size of display screen 104 enables viewing information and drug names of significant length. In some embodiments, certain commands or instructions are not controlled by a touchscreen such as display screen 104 but instead are controlled by keypad 106.

Keypad 106 is located adjacent to display screen 104 and presents a variety of buttons and indicator lights. In some embodiments, push buttons requiring physical mechanical actuation are used on keypad 106 for certain user commands, including: on/off power; audible alarm mute; start infusion; and stop infusion. Additional or fewer buttons on keypad 106 are contemplated as well. Physical mechanical actuation buttons, for primary or redundant purposes, provide increased safety and reliability to operators in cases where the touchscreen of display 104 does not function properly, or is otherwise difficult to manipulate correctly. Having a user interface 102 including both a display screen 104 and a keypad 106, accordingly, provides the flexibility of a screen interface as well as the enhanced safety and reliability of physical control buttons. In embodiments, keypad 106 comprises control buttons that operate functionally in tandem with display screen 104.

Figure 3:
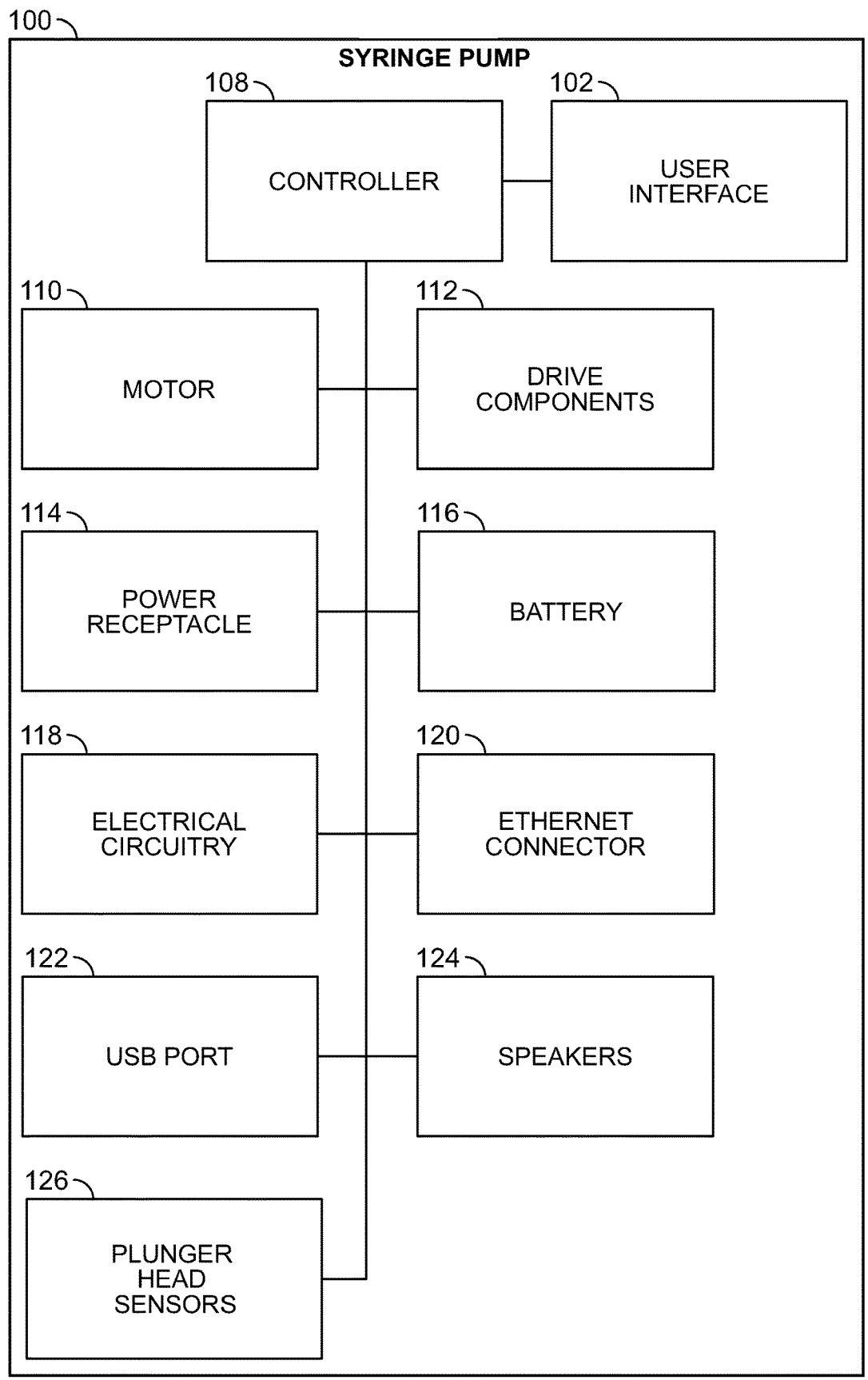
FIG. 3 is a system diagram of an infusion pump comprising a syringe pump, according to an embodiment.

Referring to FIG. 3, a system diagram of pump 100 is depicted, according to an embodiment. FIG. 3 illustrates a syringe pump 100 including user interface 102, a controller 108, a motor 110, drive components (drivetrain) 112, a power receptacle 114, a battery 116, electrical circuitry 118, an Ethernet connector 120, a USB input port 122, speakers 124, and plunger head sensors 126.

As will be described, pump 100 and/or its components or subsystems can include a processor or multiple processors. In an embodiment, the processor(s) discussed herein can be any programmable device that accepts digital data as input, is configured to process the input according to instructions or algorithms, and provides results as outputs. In an embodiment, the processor(s) discussed herein can be configured to carry out the instructions of a computer program. Processors and other such devices discussed herein are therefore configured to perform basic arithmetical, logical, and input/output operations.

Pump 100 and/or its components or subsystems discussed herein can include memory. Memory can comprise volatile or non-volatile memory as required by the coupled processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the invention.

The components described herein can be constructed, programmed, configured, or otherwise adapted, to autonomously carry out a function or set of functions. Various components can comprise a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that implement the particular functionality, which (while being executed) transform the microprocessor system into a special-purpose device. Components also be implemented as a combination of the two, with certain functions facilitated by hardware alone, and other functions facilitated by a combination of hardware and software. Accordingly, each component can be realized in a variety of physically embodied configurations, and should generally not be limited to any particular implementation exemplified herein, unless such limitations are expressly called out. In addition, a component can itself be composed of more than one sub-component, each of which can be regarded as a component in its own right. Moreover, in the embodiments described herein, each of the various components corresponds to a defined autonomous functionality; however, it should be understood that in other contemplated embodiments, each functionality can be distributed to more than one component. Likewise, in other contemplated embodiments, multiple defined functionalities may be implemented by a single component that performs those multiple functions, possibly in parallel or series with, and/or complementary to other functions, or distributed differently among a set of components than specifically illustrated in the examples herein.

As discussed above, user interface 102 serves as a source of data input for pump 100 from a medical practitioner, pump programmer, or other user. User interface 102 can include a touchscreen display 104, keypad 106 or a combination of these or other user interface technologies. In embodiments, as will be described, user interface 102 can further include a display controller subsystem (see FIG. 4).

Controller 108 is connected to the user interface and is responsible for ensuring that the pump 100 is controlled in the desired manner. Controller 108 is located in the housing 212 and controls operation of the motor 108 and drive components 108. In certain embodiments, controller 108 further controls operation of user interface 102. For example, the display controller subsystem can implemented within controller 108, or be separate from controller 108 in other embodiments. Controller 108 can include one or more processors. Controller 108 may further include memory in some embodiments.

Motor 110 is operable coupled to controller 108 and pump components generally. Motor 110 is the primary means for directing drivetrain 112 (or drive components) to effect movement of a plunger head assembly. Drivetrain 112 can be a set of drive components that are at least partially located in the housing of the pump and which are responsible for mechanically directing infusion of fluid.

Pump 100 further includes either line power via a cord connected to power receptacle 114 or via a connector in a rack that connects to power receptacle 114. Battery 116 provides another alternate source of power to the infusion pump 100. Battery 116 can be fully enclosed in the housing, in embodiments.

Various electrical components and electrical circuitry 118 are located within the pump housing that are required for relaying or carrying out commands to controller 108 or within the system. Various outside devices may be connected to pump 100 as well through inputs, such as Ethernet connector 120 or USB port 122.

Speakers 124 are equipped to provide a full range of audio outputs including commands, alerts, and informative communications.

Plunger head sensors 126 and other sensors can be part of the system as well. Plunger head sensors 126, for example, can make various measurements for tasks such as characterizing syringes, detecting occlusions, and determining plunger position. Controller 108 utilizes information gained from sensors 126 and other components to assist in communications and decision-making. Although not specifically illustrated, it is to be appreciated and understood that in LVP pump embodiments, sensors 126 can comprise sensing devices for LVP applications.

Figure 4:
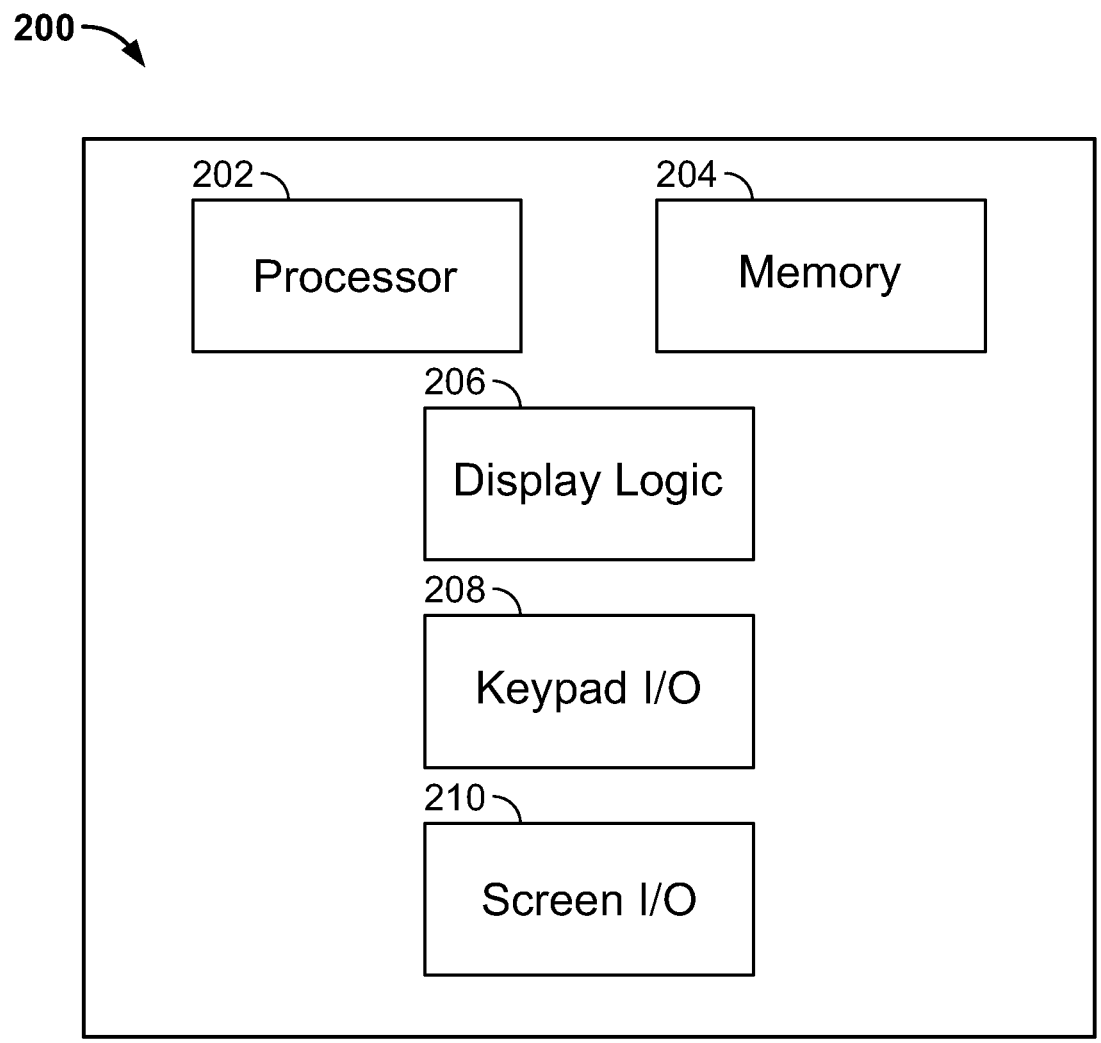
FIG. 4 is a controller display subsystem for an infusion pump, according to an embodiment.

Referring to FIG. 4, a controller display subsystem 200 for an infusion pump is depicted, according to an embodiment. Controller display subsystem 200 can be implemented as part of controller 108 and/or user interface 102. In other embodiments, controller display subsystem 200 can be implemented separate from controller 108. Controller display subsystem 200 generally comprises a processor 202, a memory 204, display logic 206, keypad I/O 208, and screen I/O 210.

Processor 202 comprises a programmable device configured for display and user interface operations.

Memory 204 is operably coupled to processor 202 and can provide space to execute the instructions or algorithms of display logic 206, and can also provide the space to store the instructions themselves, in certain embodiments.

Display logic 206 comprises software logic configured to make logical decisions about what information to display to a user. In embodiments, display logic 206 can receive inputs from keypad I/O 208 and/or screen I/O 210. Further, display logic 206 can be integrated with controller 108 and the infusion algorithms for pump 100. In an embodiment, information received by display logic 206 is used to determine what is displayed to a user via screen I/O 210. The user interfaces commanded by display logic 206 for syringe pumps and LVPs can be identical, with possibly some exceptions. For example, the screens that address loading "disposables" are customized for syringes and LVP cassettes. As referenced throughout this document, the term "disposable" is intended to include, but not be limited to a disposable syringe or a disposable, collapsible bag reservoir, or disposable infusate lines and tubing sets. In another example, a syringe pump display has screens for confirming and priming the syringe. In another example, some infusion parameters and alarm conditions are unique to a syringe pump while others are unique to an LVP.

Keypad I/O 208 comprises a plurality of buttons and indicator lights similar to keypad 106 in FIGS. 1-2.

Screen I/O 210 comprises a generally rectangular, color, LCD screen, and can be a touchscreen similar to display screen 104 in FIGS. 1-2. Screen I/O 210 can display outputs, status, alerts, and other pump-related information. Likewise, screen I/O 210 can receive user input via touch command. In embodiments, single tap is the only input gesture recognized by the touchscreen. In such embodiments, screen I/O 210 does not recognize double tap, tap and hold, swipe, or pinch gestures. When a user taps the screen, input is recognized by the pump on release of the finger, not on the press of the finger. When a user enters alpha or numeric characters into a text field, content in the text field is recognized when the field loses focus. A field in focus loses focus when another area of the screen is tapped. When a tap on a touch target results in launching a new screen, there is a brief time period during which user input is not accepted. The purpose is to minimize the effect of an accidental double-tap resulting in tapping a touch target on the next screen, and to avoid inadvertent "touches" caused by liquid droplets on screen I/O 210.

User Interface Basics

According to embodiments, screen I/O 210 can generate a number of basic screen types. For example, a Splash screen comprises an initial screen displayed at power on, while the pump performs power up and self-test processes. In an embodiment, the Splash screen includes a background graphic and product information. In another embodiment, a Menu screen comprises a grid of items that can be selected by the user by touching or otherwise choosing a portion of screen I/O 210. In another embodiment, an Edit screen comprises a virtual keypad and text fields that accept input from the virtual keypad. Program parameters can be input through the virtual keypad. Further, some other message screen types also can require data entry using the virtual keypad. In another embodiment, a View screen is configured to display non-editable parameters, such as a Ready-to-Start indication. In another embodiment, a Search screen comprises a keyboard for searching for protocols. In another embodiment, an Options screen comprises a menu of user-settable options and settings. In another embodiment, a Message screen comprises a secondary screen that overlays a main screen. In another embodiment, a Report screen comprises a generic reporting interface. In another embodiment, an Infusion Status screen comprises a non-editable screen configured to display infusion status and other information relating to an infusion.

Figure 5:
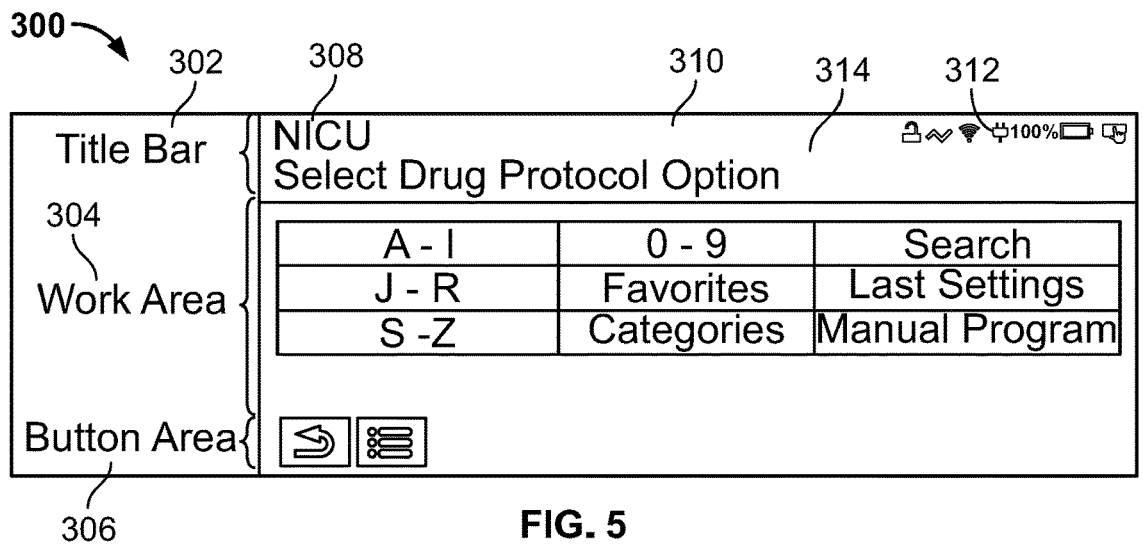
FIG. 5 is a screenshot of an example infusion pump touchscreen menu depicting a title bar, work area, and button area, according to an embodiment.

Referring to FIG. 5, a screenshot of an infusion pump touchscreen menu illustrating example screen areas of a title bar area 302, a work area 304, and a button area 306 is depicted according to an embodiment.

In an embodiment, title bar 302 can comprise two types: an Infusion Title Bar and a Programming Title Bar. In an embodiment, the Infusion Title Bar can be displayed on Near Run and Far Run screens, as will be described. In an embodiment, the Programming Title Bar can be displayed on all other screens except the Splash Screen and Message screens. In an embodiment, both types of title bar 302 have four regions where information is displayed. For example, the four regions can include a profile region 308 (e.g. "NICU" in FIG. 5), an alarm indication region 310 adjacent to profile region 308, a status indication region 312 adjacent to alarm indication region 310 (e.g. lock button, WIFI indication, battery icon in FIG. 5), and a screen title/drug protocol name (hereinafter "screen title") region 314 (e.g. "Select Drug Protocol Option" in FIG. 5). In an embodiment, both title bars 302 comprise two rows with the same background color. A top row can display the profile, alarm indications, informational alerts and status icons. For programming title bars, a bottom row can include a screen title or drug protocol/drug name. For infusion title bars, a bottom row can include infusion status.

The screen areas displayed for the above-described basic screen types are described in Table 1.

TABLE 1

| Screen Type | Screen Area | | |
|---|---|---|---|
| | Title Bar | Work Area | Button Area |
| Splash | No | Yes | No |
| Menu | Yes | Yes | Yes |
| Edit | Yes | Yes | Yes |
| View | Yes | Yes | Yes |
| Search | Yes | Yes | Yes |
| Options | No | Yes | Yes |
| Message | No | Yes | Yes |
| Report | No | Yes | Yes |
| Infusion Status - Near Run Screen | Yes | Yes | Yes |
| Infusion Status - Far Run Screen | Yes | No | No |

Profile region 308 is configured to display a profile selected by the user. For example, a profile can be selected via an Edit screen type. If no profile is selected, profile region 308 can be left blank. In certain embodiments, a profile is not displayed while an Alarm Indication or Informational Alert is displayed, as such indications take over the Profile Area while they are active, as will be described.

Alarm indication region 310 is configured to display alarm indications and informational alerts. Alarm indications can include visual indications of an alarm condition, such as a brief description of the alarm with color-coded backgrounds and a standard alarm priority symbol to represent alarm priority, and an Additional Information icon if there is additional information available to be displayed in an Alarm Message Screen. In an embodiment, the alarm priority symbol is compliant with IEC 60601-1-8 ed2.1

Consol. with am1 (2012-11). Alarm indication region 310 elements are described in Table 2, according to an embodiment.

TABLE 2

| Alarm Priority | Title Bar Background Color | Title Bar Text Color (including alarm priority symbol and status icons) | Alarm Priority Symbol |
|---|---|---|---|
| High | Red | White | △ |
| Medium | Yellow | Black | △ |
| Low | Yellow | Black | △ |

When an alarm condition is triggered, the background color of the title bar changes to represent the priority of the alarm. Further, the text in the title bar 302 (for Programming title bars) or the infusion state (for Infusion title bars) is displayed in a smaller font size. In an embodiment, alarm indication region 310 "takes over" profile region 308 and/or screen title 314 such that the previously-displayed infusion profile is no longer displayed. In certain embodiments, alarm indication region 310 content is displayed in a larger font size.

Figure 6A:
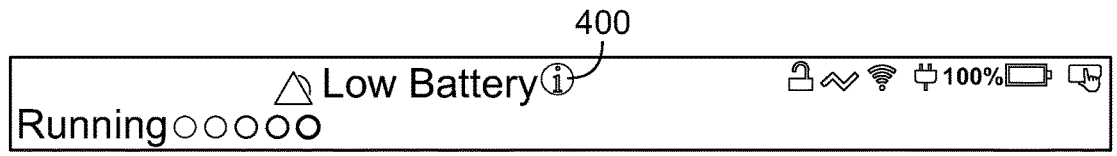
FIGS. 6A-6C are screenshots of example infusion pump touchscreen display title bars with alarm indications for low, medium, and high-priority alarms, according to embodiments.
Figure 6B:
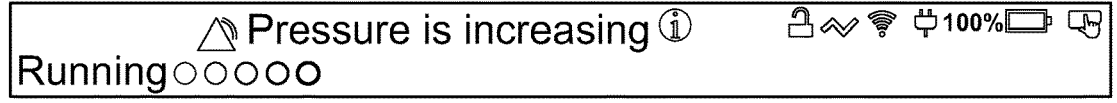
Figure 6C:
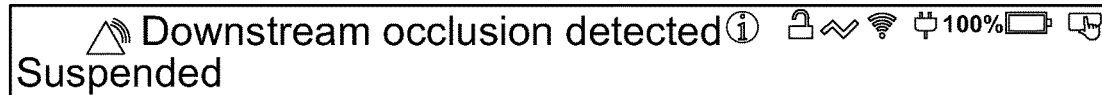

For example, FIG. 6A is a screenshot of an infusion pump touchscreen title bar with a low-priority alarm, according to an embodiment. FIG. 6B is a screenshot of an infusion pump touchscreen title bar with a medium-priority alarm, according to an embodiment. FIG. 6C is a screenshot of an infusion pump touchscreen title bar with a high-priority alarm, according to an embodiment.

In an embodiment, only one alarm indication is displayed at a time. A higher priority alarm indication replaces a lower priority alarm indication. If more than one alarm is active at a given time, the alarm indications are displayed in priority order one after the other as each alarm is resolved.

Figure 7:
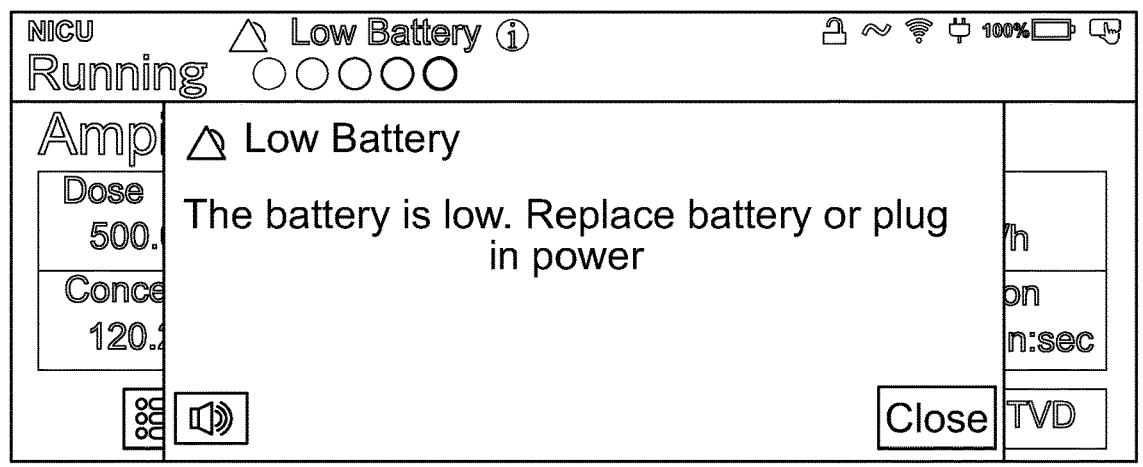
FIG. 7 is a screenshot of an infusion pump touchscreen alarm message screen, according to an embodiment.

A user can tap an additional information icon on the touchscreen, such as an information ("i") icon 400 in FIG. 6A, to view additional information on an alarm message screen. FIG. 7 is a screenshot of an infusion pump touchscreen alarm message screen, according to an embodiment. In embodiments, a touch target for launching the alarm message screen is not limited to icon 400. Tapping anywhere on the touchscreen in alarm indication region 310 launches the alarm message screen, which provides additional details about the alarm and, if applicable, instructions for correcting the condition that triggered the alarm.

Figure 8:
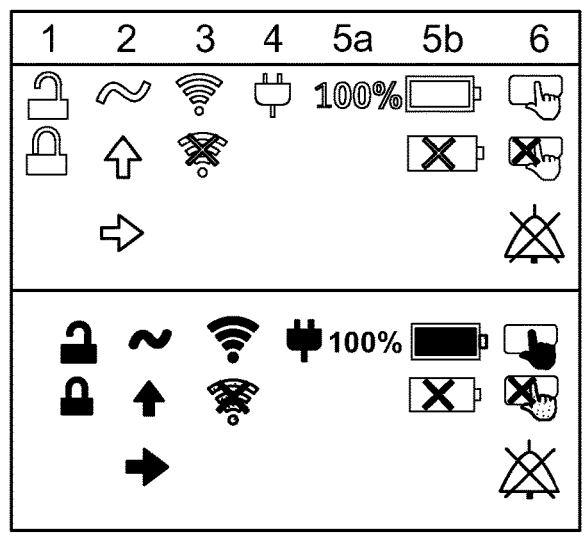
FIG. 8 is a collection of status icons for a status indication region of a user interface for an infusion pump, according to an embodiment.

Status indication region 312 is located on the right side of title bar 302 and displays icons that indicate pump and infusion status. In an embodiment, referring to FIG. 8 and Table 3, various status indicators can reflect various functional elements of the infusion pump. For example, referring to FIG. 8, each column of icons represents the status icons and their various states. Icons can remain in their assigned positions whether or not all icons are displayed. If an icon is not displayed, its position is left blank. Table 3 below describes various icon behaviors. In an embodiment, status icons are white except when the title bar background color is yellow (low and medium alarm indication is displayed). When the title bar background color is yellow, status icons are black.

TABLE 3

| Name | Description | State | Icon | Meaning |
|---|---|---|---|---|
| Secure Protocol | Indicates whether a secure profile has been selected and, if a secure protocol has been selected, the locked/unlocked state | Unlocked | 🔓 | Secure protocol parameters are available for editing |
| | | Locked | 🔒 | Secure protocol parameters are not available for editing |
| | | No secure protocol selected | No icon displayed | There is no profile selected or the selected profile is not a secure profile |
| Pressure Sensor | Indicates the status of the pressure sensor system | Stabilizing | ~ | Pressure is stabilizing |
| | | Increasing | ↑ | Pressure is increasing. |
| | | Stable | → | Pressure is stable. |
| | | Not enabled | No icon displayed | Pressure sensor is not enabled for use. |
| Server Connection | Indicates that the pump is connected to the server (via wireless or LAN connection). | Connected to server | 📶 | Pump is connected to server via Wi-Fi or wired network connection. |
| | | Pump is not connected to server. | No icon displayed | Pump is not connected to server |
| Wireless | Indicates whether wireless is on or off. | Wireless on | No icon displayed | Wireless is turned on |
| | | Wireless off | ✕ | Wireless is turned off |
| AC Power | Indicates whether pump is running on external power | Externally Powered | ⚡ | Pump is powered by an external power source. |
| | | Not Externally powered | No icon displayed | Pump is not powered by an external power source. |
| Battery Charge Value | Numeric indication of battery charge level (percent charged to the nearest 1%) | Changes to reflect battery charge level. | 100% | Displays numeric battery charge level to the nearest 1% (as text or a series of icons) |
| Battery Charge | Graphic indication of | | ▭ | Filled in portion of the |

TABLE 3-continued

| Name | Description | State | Icon | Meaning |
|---|---|---|---|---|
| Status | battery charge level. Displays full/empty battery in 20% increments | | | battery icon represents battery charge level as described in 'notes'. |
| Defective battery | Represents defective battely. | | | Defective battery |
| Touchscreen Lock | Indicates whether touchscreen is locked. Toggles locked/unlocked state. | Unlocked Locked | | Touchscreen accepts touch input. Touchscreen does not accept touch input except in the status icon area of the Title Bar. |
| Alarm silence | Indicates that the audible alarm indication for the indicated alarm has been temporarily silenced. | Indicated alarm, alarm silence period is active | | See state |
| | | There is no alarm condition or Alarm Silence has timed out and audible alarm is sounding | No icon displayed | See state |
| Alarm off | Indicates that one or more alarms have been turned off | One or more alarms are turned off | | See state |
| | | No alarms are turned off | No icon displayed | See state |

Referring again to FIG. 5, screen title region 314 is configured to display the title of the screen. In another embodiment, screen title region 314 can display an infusion profile, except when an alarm indication is displayed or the default (factory set) profile is operating. For example, in an embodiment of a Programming Title Bar, screen title region 314 is configured to display the general "purpose" of the screen. In Programming Title Bar embodiments, screen title region 314 can also display the infusion profile, except when an alarm indication is displayed or there is only the default (factory set) profile. In another example, for an Infusion Title Bar embodiments, screen title region 314 is configured to display the infusion state and the delivery segment when appropriate. Screen title region 314 can also display the infusion profile, except when an alarm indication is displayed or the default (factory set) profile is operating.

Figure 9:
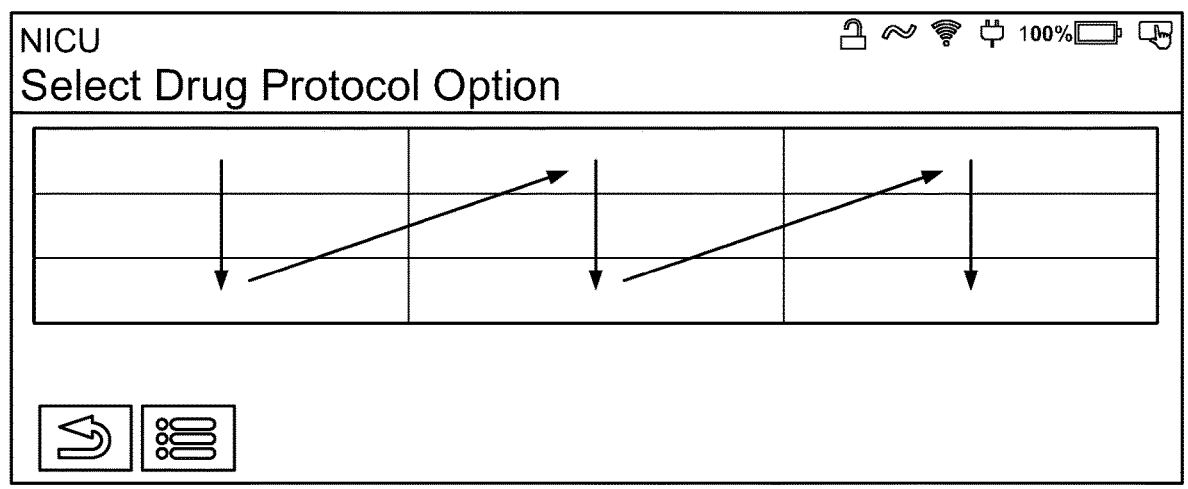
FIG. 9 is a screenshot of a grid layout for an infusion pump touchscreen menu, according to an embodiment.

With further reference to FIG. 5 and the illustrated example screen areas, work area 304 comprises the specific contents of the screens and changes depending on function. In certain embodiments, some elements, such as the design and position of a keypad, are constant across screens. In an embodiment, menu items are displayed in a grid of columns and rows. For example, referring to FIG. 9, the order of menu items is left column, top row to bottom row, then the next column to the right, top row to bottom row, etc. This type of menu grid offers the user an intuitive and readable display.

Button area 306 comprises navigation, function, and menu buttons, such as a "Back" button and "show menu" button. Navigation and menu buttons can be common across screens, with certain exceptions due to the function of the screen, as is depicted and described herein.

User Interface Security

Referring again to FIG. 4, embodiments of display logic 206 can implement inadvertent touch lock protection. Inadvertent touch lock algorithms are designed to protect the touchscreen display from inadvertent touches. Inadvertent touch lock protections can be enabled or disabled for a particular pump or set of pumps by a hospital, care area, or super user, in embodiments.

Figure 10:
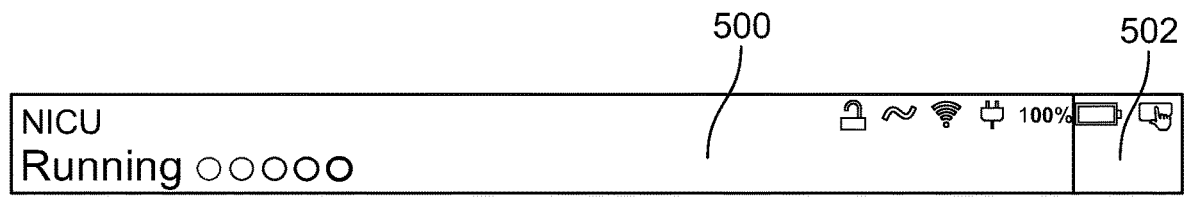
FIG. 10 is a screenshot of an infusion pump touchscreen title bar including a lock/unlock touch target, according to an embodiment.

For example, referring to FIG. 10, a screenshot of an infusion pump touchscreen title bar 500 including a lock/unlock touch target 502 is depicted, according to an embodiment. A user can lock the touchscreen at any time by tapping lock/unlock touch target 502 in title bar 500. When the touchscreen is locked, the display is still visible. The display does not have a disabled appearance, in embodiments. When locked, the only area of the screen that accepts touch input is the touch target (lock/unlock touch target 502). Lock/unlock touch target 502 can be 70×64 pixels, which has the same dimensions as a key on touchscreen numeric keypad, in embodiments.

In certain embodiments, while there is a status icon that indicates that the screen is locked or unlocked, there is no visual indication of how to lock or unlock the screen. Further, in embodiments, if an alarm occurs while the screen is locked, the screen remains locked. An Alarm Indication in title bar 500 can be presented. The user can silence the alarm with an alarm silence button on the physical keypad button, such as keypad 106.

In manual locking and unlocking operation, when for example the user touches lock/unlock touch target 502 as depicted in FIG. 10, the touchscreen is locked and lock/unlock touch target 502 changes to a locked indication. Touch response is then disabled. If the user touches in any area other than lock/unlock touch target 502, touch is ignored. To unlock the touchscreen, the user can tap lock/unlock touch target 502. Touch response of the rest of the touchscreen is then enabled.

Figure 11:
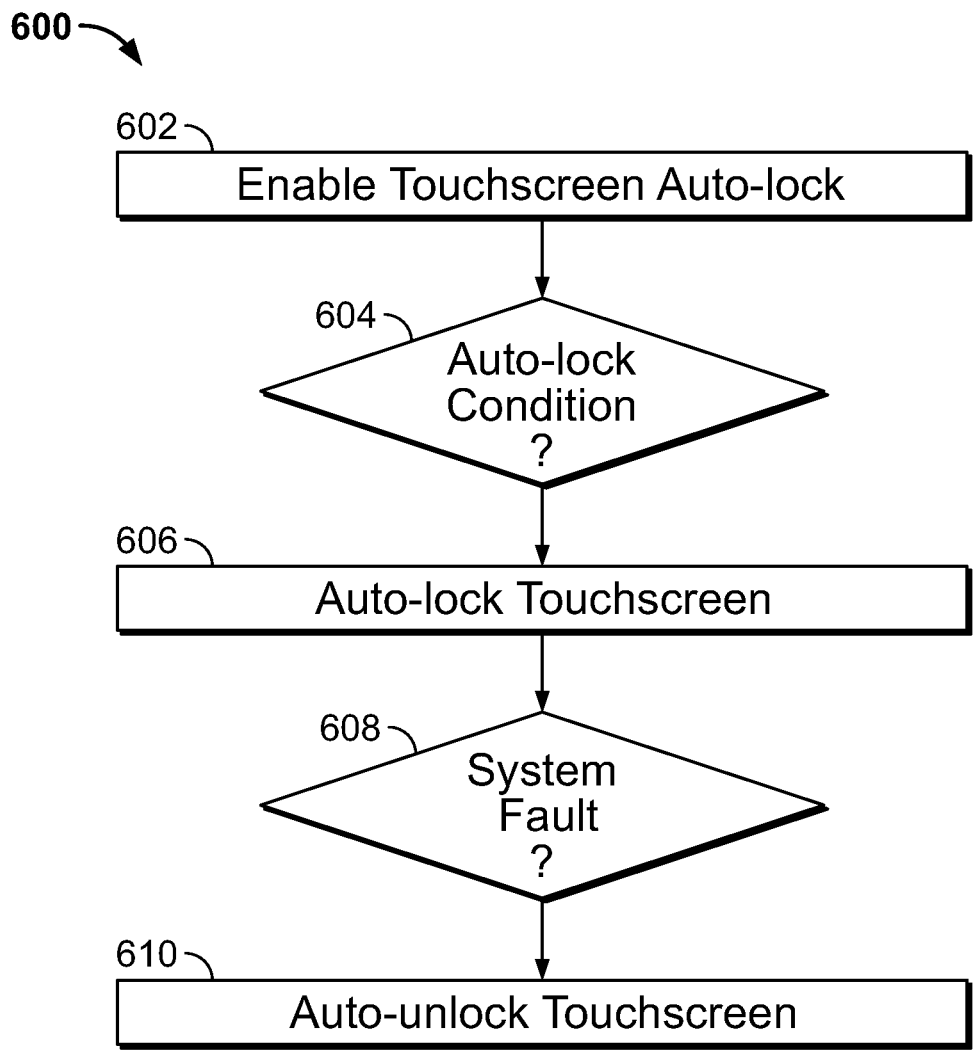
FIG. 11 is a flowchart of a method for providing inadvertent touch lock for an infusion pump touchscreen display, according to an embodiment.

Automated methods for locking and unlocking the touchscreen are also disclosed herein. Referring to FIG. 11, a flowchart of an automated method 600 for providing inadvertent touch lock for an infusion pump display screen is depicted, according to an embodiment. In embodiments, method 600 provides automatic locking and unlocking based on certain conditions.

For example, at 602, touchscreen auto-lock is enabled. Touchscreen auto-lock can be enabled according to site, practice or care area, or by individual pump, in certain embodiments. For example, touchscreen auto-lock can be enabled for an entire hospital. In another example, a hospital may want touchscreen auto-lock enabled for a pediatric care area, but not for an emergency care area.

At 604, an auto-lock condition is checked. For example, an auto-lock condition can comprise a check for an infusion that is starting. In this example, when the infusion starts, the screen is viewable but is immediately locked. Display logic can detect when the physical start button is pressed and correspondingly lock the screen. In another example, an auto-lock condition can comprise a time duration check for activity with the pump touchscreen. For example, a timer can be started after the "last" touch on the touchscreen. Once the timer has reached a certain threshold, the touchscreen can be locked.

At 606, as described, the touchscreen is automatically locked if one of the auto-lock conditions is met.

At 608, an auto-unlock condition is checked. For example, as depicted in FIG. 11, if a system fault occurs, the touchscreen is automatically unlocked, as this condition is potentially dangerous to the patient and no time should be wasted by the user to unlock the touchscreen. In other embodiments, the touchscreen can be automatically unlocked if another auto-unlock condition is met.

At 610, as described, the touchscreen is automatically unlocked if one of the auto-unlock conditions is met. In certain embodiments, the touchscreen does not auto-unlock when an alarm condition occurs, as described above with respect to FIG. 10.

User Interface Operation

Referring to FIGS. 12A-12B, 13A-13C, and again to FIG. 4, display logic 206 can command processor 202 to display certain screens based on operation characteristics. For example, referring specifically to FIG. 12, a flowchart of a method 700 for displaying a near-run screen or far-run screen for an infusion pump display screen is depicted, according to an embodiment. An example near-run screen is depicted in FIG. 13B, according to an embodiment. An example far-run screen is depicted in FIG. 13C, according to an embodiment.

Referring again to FIG. 12A and at 702, infusion information is received by the infusion pump. In an embodiment, basic infusion information such as a rate and a volume can be input manually into interfaces provided by screen I/O 210. In embodiments, a drug selected from a drug library along with other infusion parameters can be manually input into screen I/O 210. In another embodiment, the infusion pump can receive infusion parameters remotely from a separate computing device. The infusion pump is then programmed with the received infusion parameters.

Figure 13A:
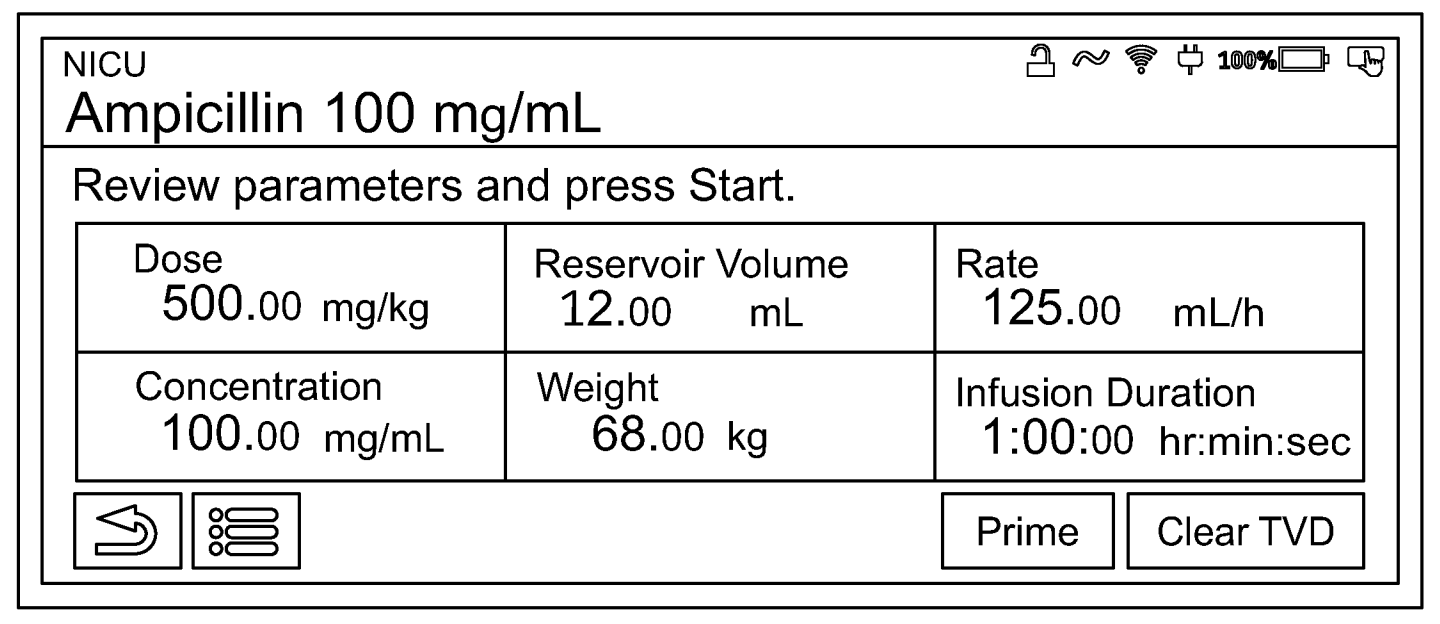

At 704, once the infusion pump parameters are programmed into the pump, a ready-to-run display is presented by screen I/O 210. An example ready-to-run screen is depicted in FIG. 13A, according to an embodiment. The ready-to-run screen summarizes certain infusion parameters in the work area, such as dose, reservoir volume, rate, concentration, patient weight, and infusion duration. The work area summary can depict infusion parameters in an easy-to-read grid format. If a user wishes to make changes, he can tap the appropriate grid space and edit that field. For example, tapping on the "Rate" box will present a rate parameter screen that a user can manipulate to edit the rate parameter. In other embodiments, pressing the "Back" button in the button area presents an all-parameters screen that a user can manipulate to edit any of the entered parameters, as will be discussed.

To initiate the infusion, the user can then be prompted to "Review parameters and press Start" as indicated in FIG. 13A. The "Start" button can be on a separate tactile button on a keypad separate from the touchscreen, such as keypad 106.

At 706, a near-run display is presented by screen I/O 210. An example near-run screen is depicted in FIG. 13B, according to an embodiment. In an embodiment, the near-run display can comprise the top 4-6 items of information, along with the drug or infusate in the work area and a "running" indication in the title bar. For example, in FIG. 13B, the near-run display includes dose, concentration, rate, and duration. The near-run display is configured to provide the user an appropriate amount of infusion pump information as if the user were relatively proximate the display. Accordingly, the user is presented relatively more information in a smaller format than if the user were at a farther distance from the display (and compared to the far-run display).

Figure 12A:
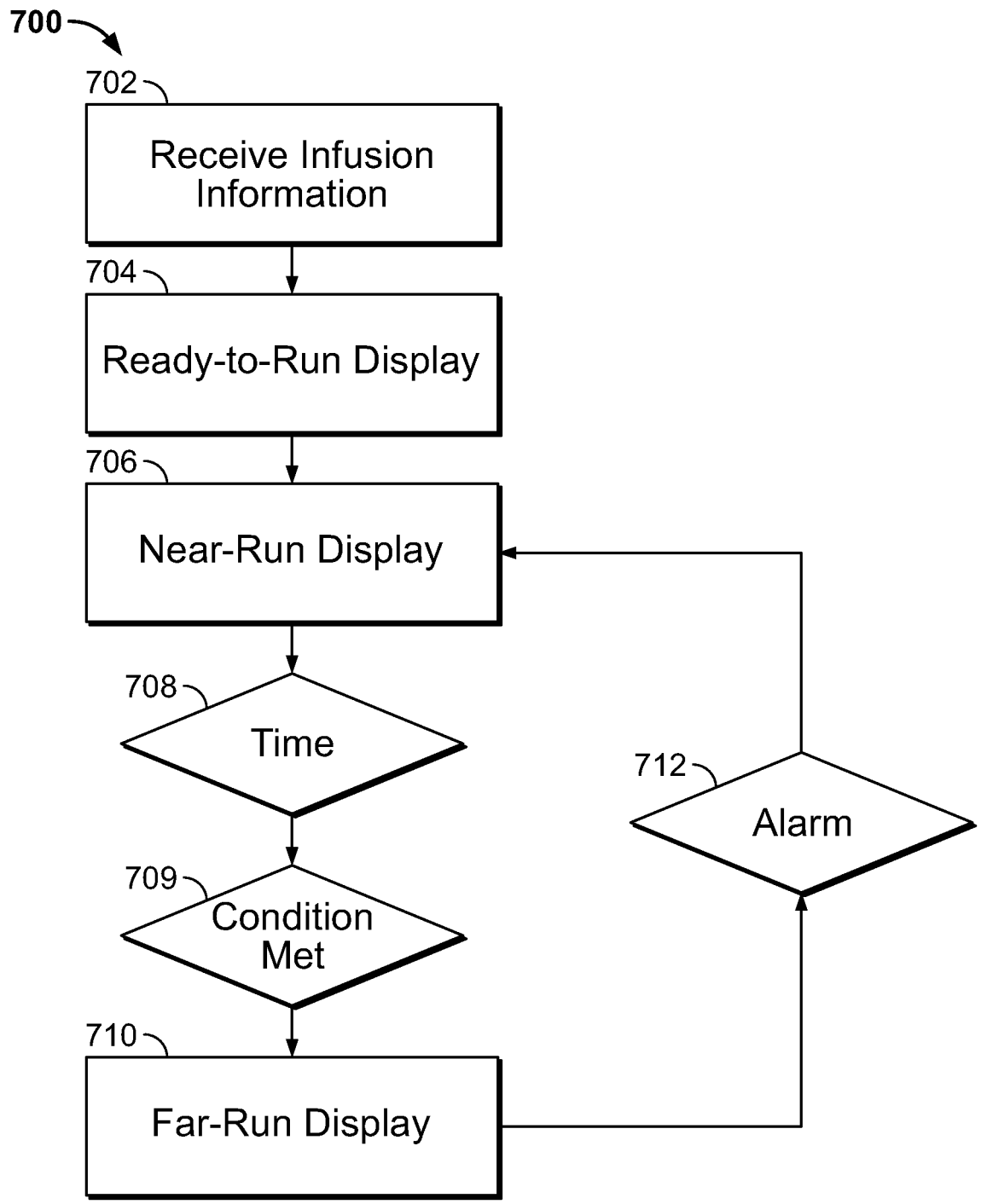
FIG. 12A is a flowchart of a method for displaying a near-run screen or far-run screen for an infusion pump touchscreen display, according to an embodiment.

At 708 in FIG. 12A, method 700 determines that time has elapsed. For example, a time counter can be utilized. The time counter can be initialized when an infusion has started. At 708, the time counter can be iteratively checked against a threshold value. The threshold value can be set at a value representing the time in the typical medical professional workflow in which the user has programmed the pump, departed from an area near the pump, and then desires to check on the pump a short time later at a distance from the pump after the infusion has been running. Other suitable trigger points to determine time can likewise be used, such as system clock data, or infusion-specific information including infusion duration or time based on infusion rate data. In an embodiment, the time elapsed threshold value can be set based on care area, particular drug, or even be pump, user, or patient specific.

In certain embodiments, with particular reference to FIG. 12A, method 700 provides a supplemental condition check at 709 in addition to time check 708 before transitioning to a far-run screen. In an embodiment, supplemental condition check 709 can include a determination if an infusion is running. In certain embodiments, an infusion can be determined to be running by checking the status or certain characteristics of the disposable. In another embodiment, supplemental condition check 709 can include a determination that a certain volume of infusate has been delivered. These types of time-supplemented evaluations at 709 provide improved control and reliability of operation compared to traditional time-based systems.

In an embodiment, supplemental condition check 709 can also act on time data. For example, it can be desirable to remain in a near-run screen for infusions that are scheduled to end soon. Therefore, in an embodiment, supplemental condition check 709 can include an elapsed time compared to an expected end time, wherein if the elapsed time is within a threshold value of the expected end time, supplemental condition check 709 is not satisfied and method 700 remains in a near-run screen. However, if the elapsed time is outside of the threshold value of the expected end time, supplemental condition check 709 is satisfied.

In an embodiment, supplemental condition check 709 determines if a bolus is currently being delivered. Due to the characteristics of certain boluses, it is advantageous to display relatively more information to the user in a near-run display (as compared to a far-run display), should the patient react in an unexpected manner during the bolus.

In an embodiment, supplemental condition check 709 can utilize proximity tracking. In embodiments, a pump can comprise a location identification element, such as an RFID tag or GPS receiver. In other embodiments, relative location can be determined by WI-FI signal strength. If a pump is determined to be in the NICU or emergency room, it may be desirable to stay on a near-run display. Therefore, supplemental condition check 709 can comprise a check of relative location. In certain embodiments, supplemental condition check 709 can comprise a location determination of a certain physical area (not necessarily a care area).

In an embodiment, supplemental condition check 709 can utilize a light, sound, or motion sensor. For example, supplemental condition check 709 can be a determination that a user has waved his hand in front of the pump to indicate he is leaving and the pump is to transition to far-run. In another embodiment, supplemental condition check 709 is a determination that a user has verbally spoken to the pump to indicate a desire to transition to far-run. In another embodiment, the gain of the screen can detect a "hover over" of the hand of a user to indicate a desire to transition to far-run. For example, International Application No. PCT/US2016/012481, entitled "Medical Device Control," describes various optical pairing systems and methods, the contents of which are fully incorporated herein by reference. In another example, International Application No. PCT/US2014/051614 entitled "Infusion Pump with Touchless User Interface and Related Methods" describes various touchless programming systems and methods, the contents of which are fully incorporated herein by reference.

At 710, once time check 708 is satisfied and supplemental condition check 709 is satisfied, a far-run display is presented by screen I/O 210. An example far-run screen is depicted in FIG. 13C, according to an embodiment. In one embodiment, a far-run screen displays relatively less information than a near-run screen, but displays the information in larger size. In another embodiment, a far-run screen displays select information in a larger size, while additional information is displayed in a small size for proximate viewing, should a user desire to return to a closer view of the touchscreen.

In an embodiment, the far-run display can comprise the top two pieces of information (e.g. dose and rate), along with the drug or infusate in the work area and a "running" indication in the title bar. For example, in FIG. 13C, the far-run display includes dose and rate. The far-run display is configured to provide the user an appropriate amount of infusion pump information as if the user was relatively distant from the display. Accordingly, the user is presented relatively less information in a larger format than if the user was proximate the display (and compared to the near-run display). Accordingly, display logic is configured to adjust the number and type of infusion pump information displayed, but also the size of infusion pump information displayed.

At 712, an alarm has been triggered at the infusion. Accordingly, method 700 proceeds to near-run display 706 in order to present relatively more information to the user, who will likely be returning to view in detail and attend to the infusion pump display due to the alarm. Once the alarm is cleared, method 700 can again proceed to time check 708 and far-run display 710 as appropriate. In certain embodiments, transitioning from a far-run display to a near-run display can be indicative of an alert or low priority alarm, such as "Network Communication Lost," where a user will likely wish to obtain additional information. Embodiments therefore provide an automatic transition for the user so he does not have to manually select the near-run display. In another embodiment (not pictured), a user can manually "tap" the far-run display to return to the near-run display. In embodiments, the far-run display does not present a particular "back" button; rather, the entire screen can receive user input to return to the near-run display. This flexibility offers advantages over traditional systems, where a user must find and press a particular area of the screen corresponding to a "back" button. Method 700 can proceed to near-run display 706 from far-run display 710 by other triggering criteria. In another embodiment, when method is presenting a far-run display, sensors can automatically sense when a user is proximate the display using, for example a proximity or light sensor. In embodiments, method 700 then presents a near-run display. Effectively, method 700 and associated steps present a near-run display from a far-run display when the user is about to return or has returned proximate the display.

Figure 12B:
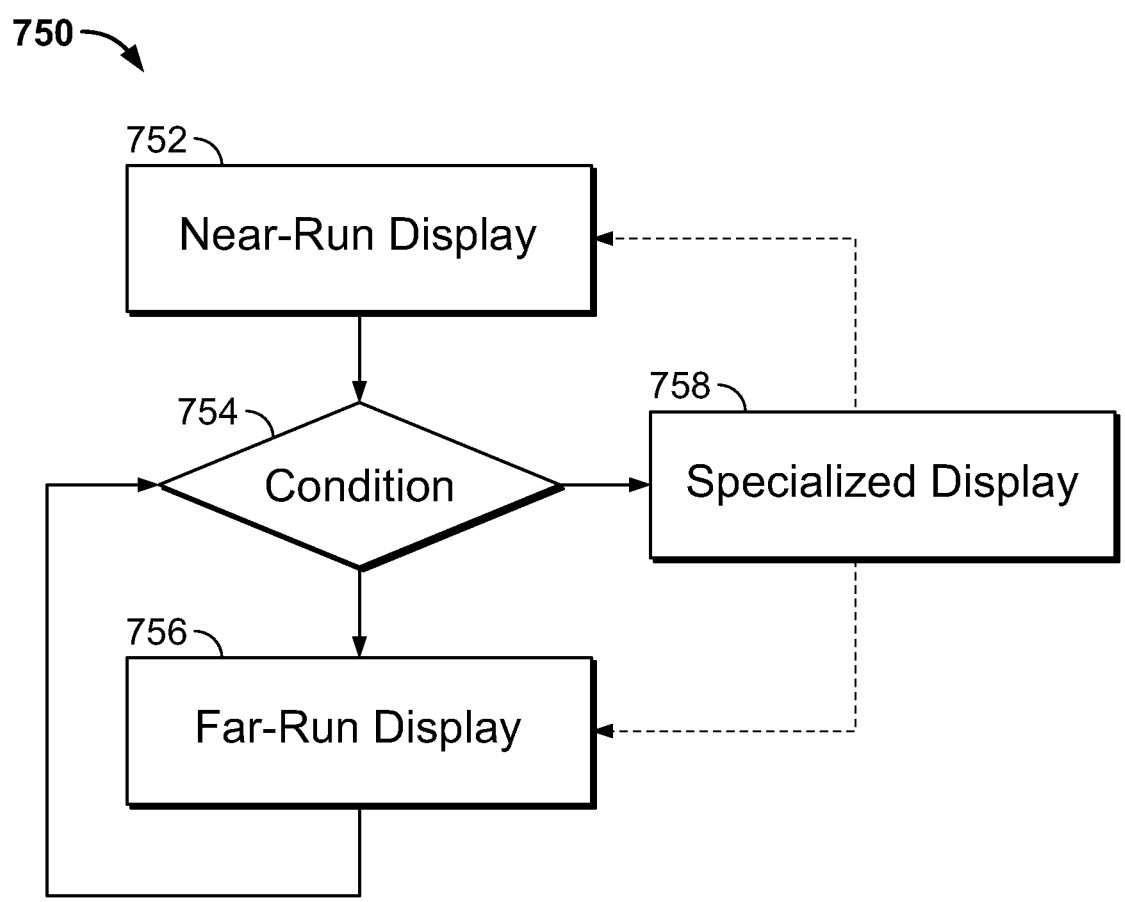
FIG. 12B is a flowchart of a method for displaying informational screens for an infusion pump touchscreen display, according to an embodiment

Referring to FIG. 12B, a flowchart of a method 750 for displaying informational screens for an infusion pump touchscreen display is depicted, according to an embodiment. Method 750 provides additional informational screens beyond the near-run/far-run displays of method 700. In certain embodiments, as will be discussed, a specialized display is presented depending on certain conditions of the infusion pump or coupled system.

At 752, a near-run display is presented by screen I/O 210. The near-run display can be substantially similar to the near-run display depicted in FIG. 13B and described above.

At 754, a condition check is conducted. In an embodiment, the condition check 754 can comprise one or more of time check 708 and/or supplemental condition check 709 as discussed with respect to FIG. 12A. In other embodiments, condition check 754 can comprise other conditional determinations. If method 750, by evaluation of 754, determines the infusion pump should transition to a far-run display, method 750 proceeds to far-run display 756.

At 756, a far-run display is presented by screen I/O 210. The far-run display can be substantially similar to the far-run display depicted in FIG. 13C and described above.

However, returning to 754 in FIG. 12B, if method 750, by evaluation of 754, determines the infusion pump should transition to a specialized display, method 750 proceeds to specialized display presentation 758. In embodiments, specialized display 758 assists the user or patient by presenting particular data, fields, parameters, graphs, etc. to better understand a current status of the infusion pump. In embodiments, the specialized display offers timely and additional information compared to a near-run or far-run display.

For example, method 750 can read flow sensor data at 754 and determine that pressure is increasing (but not yet an alarm point), where the condition at 754 is "pressure increasing." Method 750 can transition to a specialized display 758 of a pressure graph (not explicitly illustrated in the drawings) over time. In another embodiment, if the condition at 754 is determined to be "pressure increasing," method 750 can transition to a specialized display 758 of an IV bag status screen (not explicitly illustrated in the drawings).

In another example, method 750 can determine that an infusion is undergoing a rate reduction or taper at 754. Method 750 can transition to a specialized display 758 of a graph (not explicitly illustrated in the drawings) of rate behavior over time.

In another example, decision block at condition 754 can use predictive algorithms to select a specialized screen for a user. Condition 754 can determine, based on previously recorded data, a transition to given screen for a particular set of pump or system characteristics. In other words, previous transitions and the data associated with those transitions are recorded. Controller 108 can use trend lines (not explicitly illustrated in the drawings) to draw conclusions for the most desired or most often entered screen for that set of pump or system characteristics.

In another example, decision block at condition 754 can use near-field communications (NFC). In particular, a user can be proximate the pump with a phone or badge or other device having an RFID reader (not explicitly illustrated in the drawings). At 754, method 750 can determine that by the initiation of the near-field communication, the user wishes to program the pump. Accordingly, method 750 proceeds to specialized display 758, which can be a programming screen, or to near-run display 752, as appropriate.

In another example, decision block at condition 754 can determine when a peripheral device has been connected, such as a remote dose cord (not explicitly illustrated in the drawings). Accordingly, method 750 proceeds to specialized display 758, which can be a programming screen, or to near-run display 752, as appropriate. Method 750 therefore "predicts" that a user will be interacting with the pump and transitions its display appropriately.

In another example, decision block at condition 754 can use an integrated accelerometer (not explicitly illustrated in the drawings) to determine a "signature" or physical identification of a pole being "kicked" or bumped. Accordingly, method 750 proceeds to specialized display 758, which can be a "kick" alert, or to near-run display 752, as appropriate. For example, International Application No. PCT/US2015/046918, entitled "Medical Device Association Systems and Methods," describes various systems and methods for measuring spatial accelerations and for determining patterns in the accelerations, the contents of which are fully incorporated herein by reference.

From specialized display 758, method 750 can transition to near-run display 752 or far-run display 756, as appropriate. For example, if a pressure issue has been cleared or resolved, method 750 can transition to far-run display 756. However, the pressure issue has not been resolved or needs attention, method 750 can transition to an alarm state or near-run display 752. In another embodiment, if a flow sensor indicates at 754 that the infusion pump will be stopping soon, method 750 can transition from specialized display 758 back to near-run display 752.

In embodiments, once in a far-run display, method 750 can return to evaluation at 754 or a supplemental evaluation 754 to check whether method 750 is to present a specialized display 758. In embodiments, supplemental evaluation 754 can be different than the initial evaluation at 754.

Figure 14:
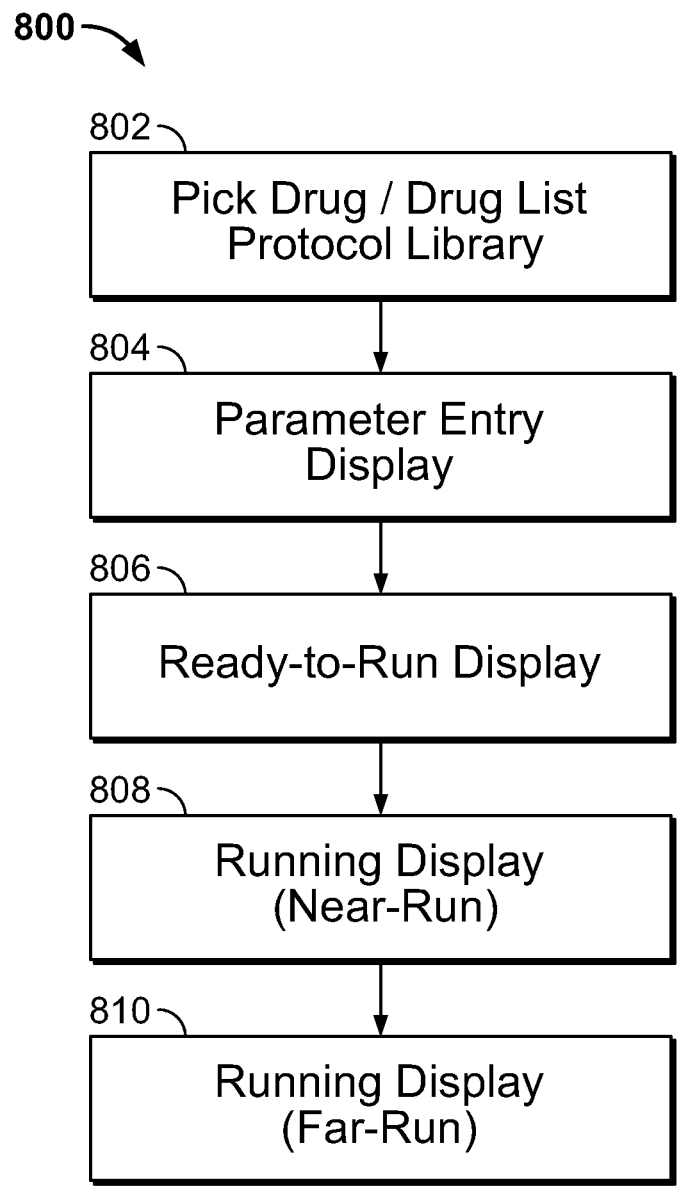
FIG. 14 is a flowchart of a method for operating an infusion pump, according to an embodiment.

Referring to FIG. 14, a flowchart of a method 800 for operating an infusion pump is depicted, according to an embodiment.

At 802, a drug or drug protocol is selected. For example, referring to FIG. 15, a screenshot of a protocol option selection screen 900 for an infusion pump touchscreen display is depicted, according to an embodiment.

Embodiments described herein provide for three-way drug lookup. Protocol option selection screen 900 allows the user to select alphabetical page lookup 902, search lookup 904, or categories lookup 906 by tapping on the appropriate icon.

Figure 15:
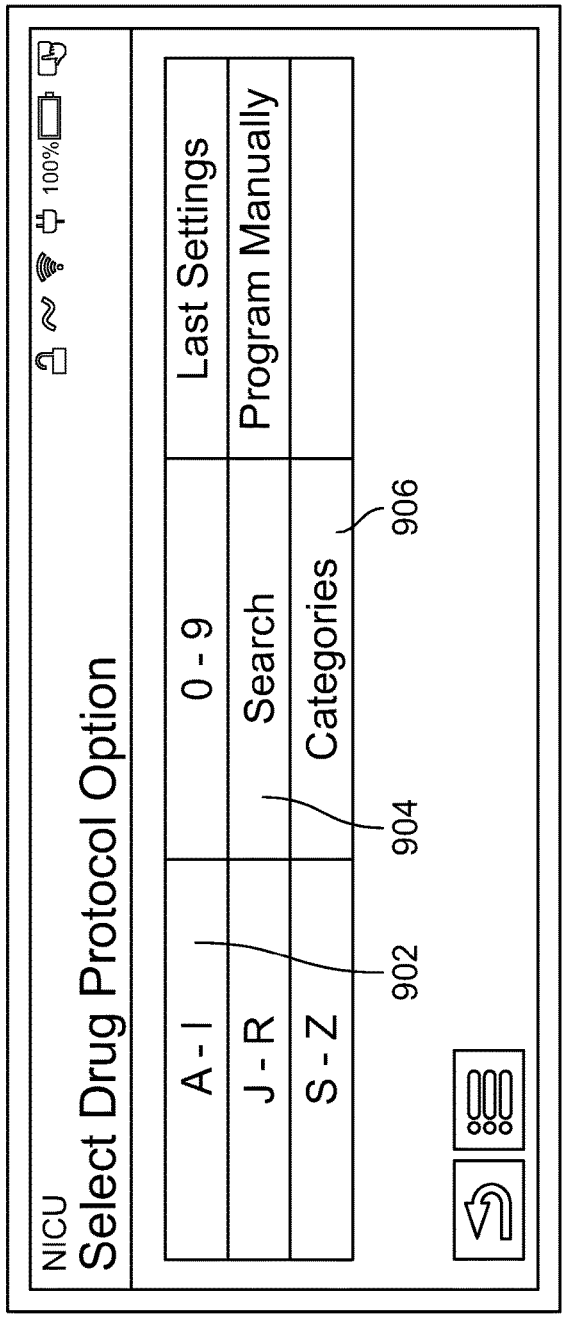
FIG. 15 is a screenshot of a protocol option selection screen for an infusion pump touchscreen display, according to an embodiment.
Figure 16:
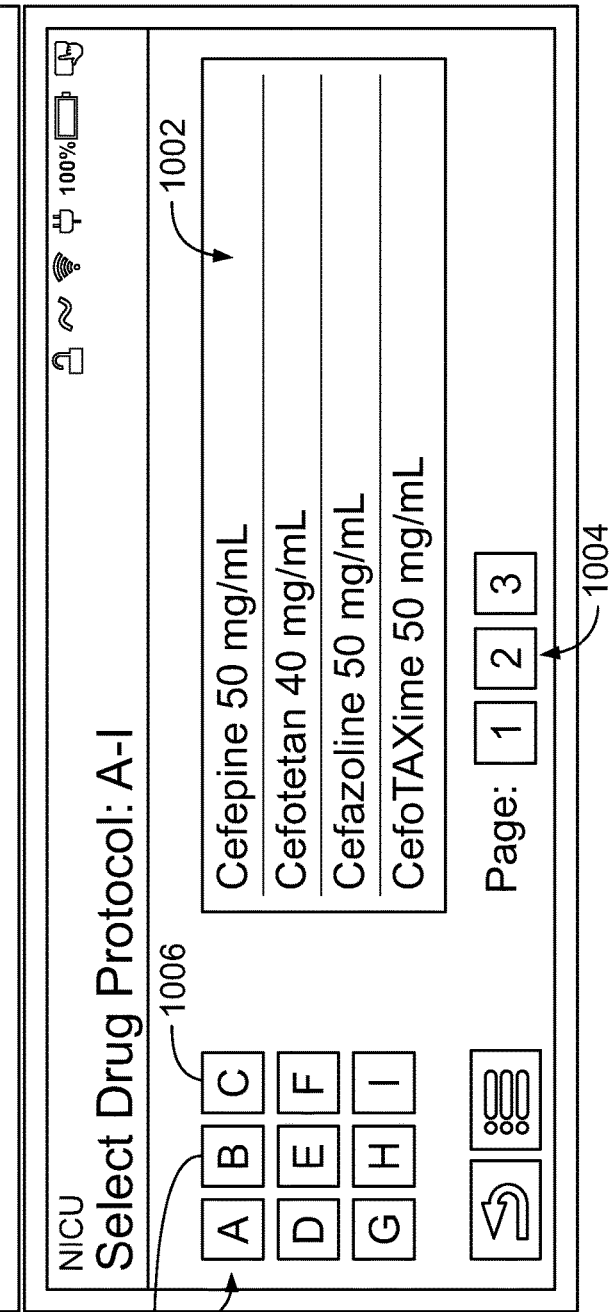
FIG. 16 is a screenshot of a drug protocol alphanumeric page lookup screen for an infusion pump touchscreen display, according to an embodiment.

Referring to FIG. 15 and FIG. 16, a screenshot of a drug protocol alphanumeric page lookup screen for an infusion pump touchscreen display is depicted, according to an embodiment. The drug protocol alphanumeric page lookup screen can be accessed by tapping the icon corresponding to alphabetical page lookup 902. In FIG. 15, alphabetical page lookup 902 is marked as "A-I" lookup, corresponding to drugs beginning with letters A-I. A user can also select "J-R," "S-Z," and numeric "0-9" to present interfaces corresponding to those alphabetical or numeric pages.

In FIG. 16, a drug protocol alphanumeric page lookup screen comprises an alphanumeric keypad 1000 corresponding to the alphanumeric range selected on the protocol option selection screen 900. For example, letters A-I are depicted each as a button for paging selection. The drug protocol alphanumeric page lookup screen further comprises a page listing 1002 corresponding to the letter selected on keypad 1000. The drug protocol alphanumeric page lookup screen further comprises a page navigation component 1004 to traverse through a plurality of pages for that letter selected. In embodiments, if all drugs fit on a single page listing 1002, no additional page navigation components 1004 are required. In contrast to traditional "scrolling" navigation, it is intuitive and easy to understand the total number of values presented in the page navigation of pages 1 to n.

In embodiments of the touchscreen interface, a button is in a selected state while a finger is being held down on that button. In an analogy to a desktop computer, a finger is being held down on a button is equivalent to a down-click with a mouse on a non-touch screen. When the finger is lifted, the action triggered by the button tap is carried out. In FIG. 16, button C 1006 is enabled and selected, while button B 1008 is "grayed-out" and disabled because there are no available protocols starting with the letter B. Throughout the various interfaces, a disabled button can represent a category or range that has no content. Once the user finds the desired drug, he can select it by tapping the appropriate row in page listing 1002.

Figure 17A:
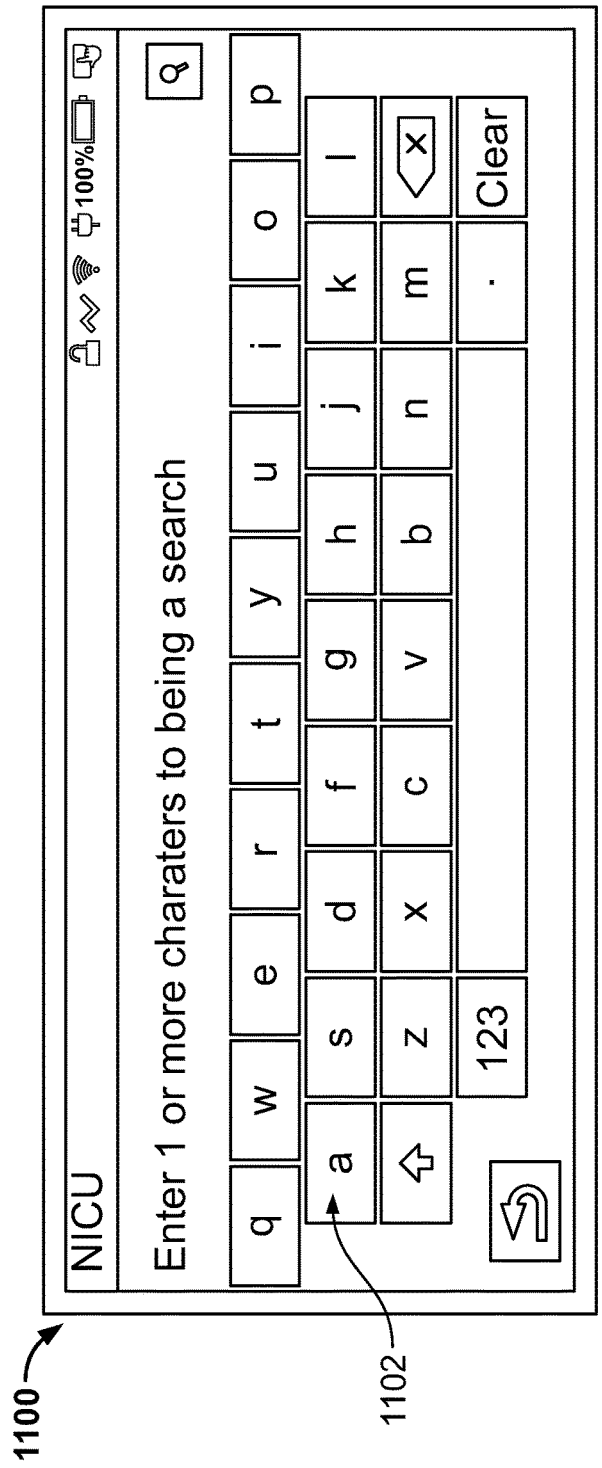
FIGS. 17A-17B are screenshots of a drug protocol search lookup screen for an infusion pump touchscreen display, according to an embodiment.
Figure 17B:
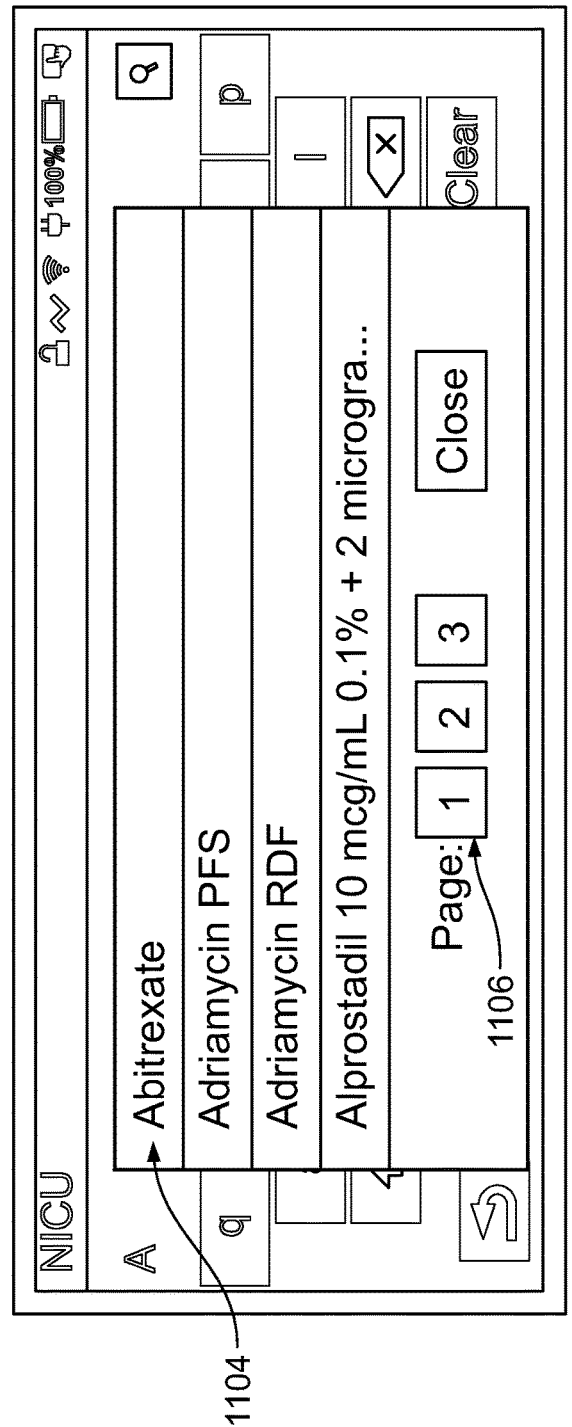

Referring to FIGS. 17A-17B, screenshots of a drug protocol search lookup screen for an infusion pump touchscreen display are depicted, according to an embodiment. The drug protocol search lookup screen can be accessed by tapping the icon corresponding to search lookup 904. After the user selects search lookup 904 on protocol option selection screen 900, an initial protocol search screen is displayed, as illustrated in FIG. 17A. Note that, referring again to FIG. 15, the user can navigate back to protocol option selection screen 900 at any point by tapping the Back button. The protocol search lookup screen generally comprises an input display area 1100 and a keyboard 1102 as depicted in FIG. 17A.

Instructions to "Enter 1 or more characters to begin a search" are initially displayed in input display area 1100. In certain embodiments, the Search button is disabled (grayed out). To utilize search lookup, the user can type search characters using keyboard 1102. Upon entering at least one character, the instruction message is removed and the display presents character input from the user. In embodiments, the Search button becomes enabled.

If the user taps the Search button at any time after typing one character, the display presents a search results listing 1104 in a page format similar to page listing 1002 in FIG. 16. If there are matches to the user's input, the display presents all matches in search results listing 1104 in FIG. 17B. Results from a drug protocol or drug name search using search lookup 904 can contain more items than can fit on one results screen. Page navigation component 1106 can likewise be utilized for search lookup results as well. If there are no matches, a "No results" message can be displayed.

Once the user finds the desired drug or infusate, he can select it by tapping the appropriate row in search results listing 1106. In embodiments, once a drug is selected, the display closes search results listing 1104, closes the drug protocol search lookup screen, and closes protocol option selection screen 900. In embodiments, the interface then automatically displays a program parameters screen.

Referring to FIG. 18, a screenshot of a drug protocol categories lookup screen for an infusion pump touchscreen display is depicted, according to an embodiment. The drug protocol categories lookup screen can be accessed by tapping the icon corresponding to categories lookup 906 in FIG. 15. The drug protocol categories lookup screen, as depicted in FIG. 18, comprises a category 1200 displayed in the title bar, with a listing of drugs 1202 for that category in the work area. Drug protocols assigned to the selected category are displayed in listing of drugs 1202. In FIG. 18, an "Antibiotics" category has been selected, and antibiotic drugs are correspondingly listed. In embodiments, the categorization of drugs can be provided by default. In embodiments, a hospital or care area can add others, if desired.

Similar to the other drug lookups, a page navigation component 1204 can be utilized for category lookup when listing 1202 contains more items than can fit on one results screen. Once the user finds the desired drug, he can select it by tapping the appropriate row in listing 1202.

Referring again to FIG. 14, at 804, after a drug is selected, a parameter entry display screen can be presented. For example, a screenshot of a program parameters screen for an infusion pump touchscreen display is depicted in FIG. 19, according to an embodiment. As will be described further with respect to FIG. 19 and the flexibility in parameter entry, all relevant parameters are presented on a single screen, or series of easily-accessible screens for user review prior to beginning the infusion.

Referring again to FIG. 14, at 806, a ready-to-run display is then presented by screen I/O 210 (with additional reference to FIG. 4). The ready-to-run screen can be similar to that described and depicted in FIG. 13A. After presentation of the ready-to-run screen, a user can start an infusion by pressing the physical "Start" button (in, e.g., keypad 106 in FIGS. 1-2).

At 808, a near-run display is then presented by screen I/O 210. The near-run display can be similar to that described and depicted in FIG. 13B.

At 810, a far-run display is then presented by screen I/O 210. The far-run display can be similar to that described and depicted in FIG. 13C. The far-run display can be automatically presented after a selected time has elapsed as described above.

Referring again to FIG. 19, a screenshot of a program parameters screen 1300 for an infusion pump touchscreen display is depicted, according to an embodiment. Program parameters screen 1300 generally comprises a plurality of fields 1302-1310, a numeric keypad 1312, a confirm button 1314, and optionally a secondary screen navigation button 1316.

Plurality of fields 1302-1308 can include dose field 1302, concentration field 1304, weight field 1306, duration field 1308, and rate field 1310. In embodiments, program parameters screen 1300 screen can contain three types of fields (e.g. fields 1302-1310), as described in Table 4 below.

TABLE 4

| Text Field Type | Description | Example |
|---|---|---|
| Editable | Text field is highlighted when the user selects the field by tapping it The user inputs a value via the numeric keyboard. Numeric input is displayed as it is entered. | Dose, Infusion Duration (If dose and infusion duration are not defined in the protocol) |
| Non-editable, predefined | The value is specified in the protocol or elsewhere during programming the infusion and is displayed in a non-editable text field. | Concentration (if concentration is defined in the protocol) Reservoir volume if it is set before the program parameters screen. |
| Non-editable, calculated | The value is calculated based on other parameter values. | Rate |

Numeric keypad 1312 can be utilized to enter numeric values into the various fields 1302-1310. Numeric keypad 1312 includes a delete button 1315, when pressed, deletes the character to the left of a cursor. When a text field containing a value is selected, tapping the back/delete key results in deletion of the rightmost character. This function can have the same effect as the Backspace key on a computer keyboard. In an embodiment, multiple characters cannot be cleared at the same time, to ensure safety and efficiency in entering parameters. Numeric keypad characters include numeric values 0-9 and a decimal point and are entered from left to right. When a field that does not take a decimal point is selected, the decimal point is blanked out or grayed-out on keypad 1312.

Confirm button 1314 is "grayed-out" or disabled until all editable fields for required parameters contain valid values. When confirm button 1314 is enabled, the checkmark icon within button 1314 turns green in color and the text word "Confirm" turns from grey to white. Color blind users should thus be able in most circumstances to visualize the contrast in colors to know that the Confirm button 1314 is now active, if they are not able to see the green check box. If there is more than one page of parameters, parameters on all pages must contain valid values before the Confirm button 1314 is enabled, as will be described. When pressed, Confirm button 1314 accepts the entered parameters and the infusion pump proceeds to a ready-to-run status.

If program parameters screen 1300 has more parameters than can fit on one screen, the parameters are displayed on multiple pages. Secondary screen navigation button 1316 is thus utilized. If there are two pages, the second page includes a "Previous" button. If there are more than two pages, the pages between the first and last pages have "Previous" and "More" buttons.

To edit a value the user has entered, the user taps the text field with the value to be edited to select it and enters a number via keypad 1312. The number replaces the entire current value. The user cannot select individual numbers in the text field for editing. Rather, the entire value is replaced. However, the user can use delete button 1315 on keypad 1312 to delete one number at a time or select the text field and tap a number on the keypad to delete the entire value at one time. If the user selects the field again for editing, this process will repeat and the current value will be cleared and the user then enters the entire number again.

Program parameters screen 1300 is depicted with both editable and non-editable text fields. For example, concentration field 1304 is non-editable because the concentration value for the infusion was provided in the protocol. Rate field 1310 is non-editable because it is calculated based on the value of other parameters. In embodiments, rate field 1310 is calculated by the pump (for example, controller 108 in FIG. 3). As soon as the parameter values needed for the rate to be calculated are entered, the pump auto-calculates and displays the rate.

Utilizing the flexibility provided by program parameters screen 1300 in which all parameters are displayed on the screen at the same time (or easily accessible subsequent screens), a user can edit any of the editable fields in any order. This contrasts significantly with traditional infusion pumps where a user was restricted to a very rigid sequence (often coupled with pressing "next" after every input, in a relatively inflexible, linearly chronological fashion, etc.).

Figure 20:
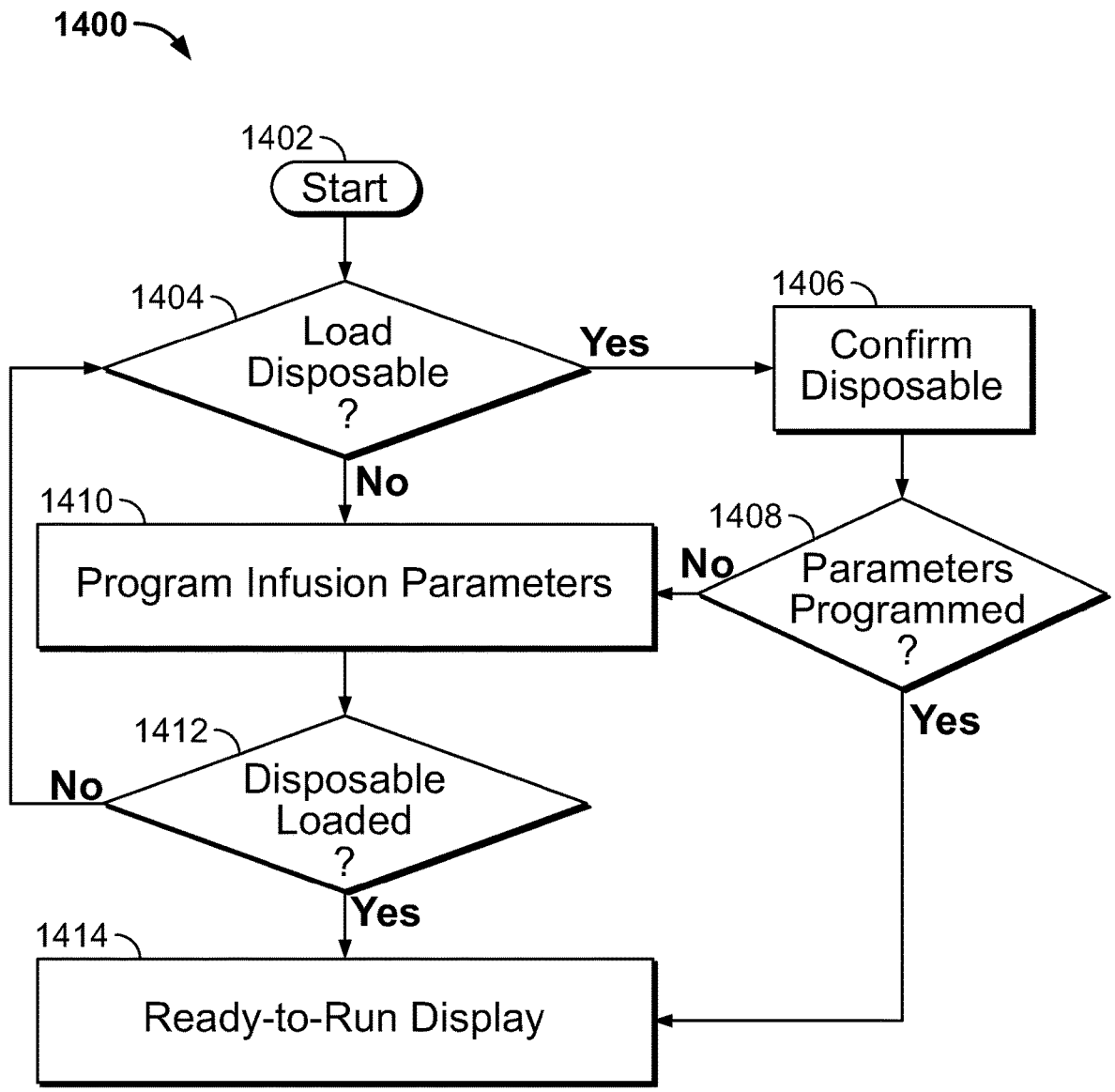
FIG. 20 is a flowchart of a method for programming an infusion pump comprising a syringe pump, according to an embodiment.

Further, embodiments provide flexible workflows in combination with the mechanical operation of the pump, such as disposable loading. For example, embodiments allow for a disposable to be loaded prior to programming infusion parameters, or certain parameters to be programmed prior to disposable loading. Referring to FIG. 20, a flowchart of a method 1400 for programming an infusion pump with a disposable is depicted, according to an embodiment.

EXAMPLE 1

Loading Disposable Before Programming Parameters

At 1402 in FIG. 20, method 1400 begins. In this particular example, at 1404, the user has decided to load a disposable prior to programming parameters (the "Yes" branch to 1406, from 1404). At 1406, the user loads the disposable and confirms the disposable is sensed by disposable sensors. At 1408, a check is made as to whether infusion parameters have been programmed. Since the disposable was loaded prior to parameters being entered, method 1400 proceeds from 1408 to programming infusion parameters at 1410. The user programs infusion parameters using, for example, program parameters screen 1300 in FIG. 19. At 1412, a check is made as to whether the disposable is loaded. In embodiments, because the disposable is already loaded prior to 1410, a variable can be set to bypass disposable loading check 1412. Method 1400 then proceeds to a ready-to-run display 1414 after the disposable has been loaded and the infusion parameters have been programmed.

EXAMPLE 2

Programming Parameters Before Loading Disposable

At 1402 in FIG. 20, method 1400 begins. In this particular example, at 1404, the user has decided to program certain infusion parameters prior to loading a disposable (the "No" branch to 1410, from 1404). At 1410, the user programs infusion parameters using, for example, program parameters screen 1300 in FIG. 19. At 1412, a check is made as to whether the disposable is loaded. Because a disposable has not yet been loaded in this example, method 1400 proceeds to load a disposable at 1404 and confirm the disposable at 1406.

In an embodiment, if a disposable has not already been loaded when the user reaches program parameters screen 1300, (or attempts to program certain parameters that will be defined by the disposable characteristics) the pump displays a Load message screen. If any disposable sensors detect movement as the user starts loading the disposable, the pump dismisses the Load message screen and displays a Sensor screen. After a disposable has been correctly loaded or removed, the pump closes the Sensor screen. The user can also close the Load message screen by tapping the Close button. In certain embodiments, the user cannot continue programming the pump until a disposable is loaded. The pump then displays the Program Parameters screen after a disposable has been correctly loaded.

In this Example 2, at 1408, a check is made as to whether the infusion parameters have been programmed. In embodiments, because the infusion parameters have already been programmed prior to 1408, a variable can be set to bypass parameters programmed check 1408. Method 1400 then proceeds to a ready-to-run display 1414 after the disposable has been loaded and the infusion parameters have been programmed.

In an embodiment, a disposable can comprise a LVP IV bag. In another embodiment, a disposable can comprise a syringe. In certain syringe embodiments, programming can be completed up to the Program Parameters screen because the size of the syringe can be necessary to provide meaningful volume and rate parameters.

Figures 21, 22:
FIG. 21 is a screenshot of a patient selection screen for an infusion pump touchscreen, according to an embodiment.
FIG. 22 is a screenshot of a quick start screen for an infusion pump touchscreen, according to an embodiment.

In an embodiment, a patient selection screen is the first screen displayed when beginning an infusion. Referring to FIG. 21, a screenshot of a patient selection screen 1500 for an infusion pump touchscreen is depicted, according to an embodiment. Patient selection screen 1500 generally comprises new patient selection 1502 and same patient selection 1504. In embodiments, as will be described, patient selection screen 1500 can further comprise quick start selection 1506.

A user can select new patient 1502 if the patient to be infused is different than the previous patient for which an infusion was made. A user can select same patient 1504 if the patient to be infused is the same as the previous infusion. This can save time for the user, in that patient characteristics and/or delivery characteristics do not need to be re-input; rather, they are simply copied over by display logic and/or the pump controller to the next infusion.

For example, patient characteristics and delivery characteristics such as patient weight, total volume infused, previous particular drugs, etc. can be captured for use in a "Same Patient" infusion. Controller 108 can store patient characteristics and delivery characteristics. In an example, controller 108 can store individual characteristics to be reused for a "Same Patient" infusion. In other embodiments, controller 108 can store a data structure associated with a particular patient ID, wherein the data structure can store multiple patient characteristics and/or delivery characteristics for that particular patient.

In an embodiment, a new patient ID is generated upon a "New Patient" infusion. As described herein, patient and/or delivery parameters or characteristics associated with that infusion can be entered by the user. Once the "New Patient" infusion is completed, such patient and/or delivery characteristics can be saved for that patient ID. As a result, upon entering the programming screens, when "Same Patient" infusion is selected, the saved parameters can be auto-populated for the subsequent "Same Patient" delivery.

In embodiments, the total volume delivered to a particular patient can be preserved using "Same Patient" infusions. This can act as a safety or reasonableness check on future infusions. For example, Medication Safety Software (along with user input) can check and allow or deny the patient additional pain medication if the patient has received an unusually large amount of intravenously-infused pain medication over the past week. In embodiments, medical professionals are provided this data to make educated treatment decisions.

In another embodiment, using "Same Patient" delivery, infusions running through power-downs can be preserved. For example, selecting "Same Patient" delivery can restart an infusion without having to re-enter all of the programming parameters for that infusion.

Referring again to FIG. 4, display logic 206 via screen I/O 210 can further provide quick start operation. For example, referring to FIG. 22, a screenshot of a quick start screen 1600 is depicted for an infusion pump touchscreen, according to an embodiment. In an embodiment, referring again to FIG. 21, an option to navigate to quick start infusion mode via quick start selection 1506 is displayed in patient selection screen 1500 as a shortcut for use when speed of getting the pump up and running is critical. Quick start infusion mode can be used without selecting a protocol or drug. Providing access to quick start mode from patient selection screen 1500 minimizes the number of steps to get the pump up and running (for example, in emergency situations).

FIG. 22 depicts one type of quick start continuous infusion mode. Quick start screen is intentionally simplified and comprises rate field 1602 and keypad 1604. The number of steps to begin infusion in quick start mode is intentionally minimized. A protocol does not need to be selected. Instead, only a rate value is required as input to rate field 1602 via keypad 1604. A user can then press "Confirm" and press Start on the tactile keypad (e.g., 106 in FIGS. 1-2) to start the infusion.

In various embodiments, the graphical user interfaces described herein are configured to accommodate long drug protocol names or long drug names ("long names"), which may not fit in the area provided. This flexibility greatly enhances safety for the patient and usability for infusion pump operators. For example, the screens listed below in Table 5 comprise a number of displays that accommodate long names.

TABLE 5

| | Screen | Select long name/View | Touch Target |
|---|---|---|---|
| 1 | Alpha Range Select Drug Protocol, | Select long name | Entire row |
| 2 | Numeric Range, Select Drug Protocol | Select long name | Entire row |
| 3 | Categories Select Drug Protocol | Select long name | Entire row |
| 4 | Search results for Protocol Search | Select long name | Entire row |
| 5 | Program Parameters | View | Display name |
| 6 | Ready To Start | View | Display name |
| 7 | Near Run | View | Display name |
| 8 | Far Run | View | Display name |

Further, decisions on when to display ellipses (" . . . ") is described in Table 6 below.

TABLE 6

| Custom Display Name | What is Displayed on Pump | Fits on Display | Truncate | Display Ellipses |
|---|---|---|---|---|
| No | Drug + Concentration | Yes | No | No |

TABLE 6-continued

| Custom Display Name | What is Displayed on Pump | Fits on Display | Truncate | Display Ellipses |
|---|---|---|---|---|
| No | Drug + Concentration | No | Yes | Yes |
| Yes | Custom Display Name | Yes | No | No |
| Yes | Custom Display Name | No | Yes | Yes |

In embodiments, it may be necessary to truncate long names. The truncation point is determined by the characters (including spaces in the display name) that can be displayed in the allotted space on the specific screen. In an embodiment, display logic commands the screen to display as many complete characters as will fit in the allotted space, and to not display partial characters at the end of the displayed string. Ellipses (" . . . ") are included in determining the number of characters that fit. On Program Parameters, Ready to Start, and Near Run screens, the truncation point is positioned to avoid accidental touch on the touch targets in the title bar.

Figure 23A:
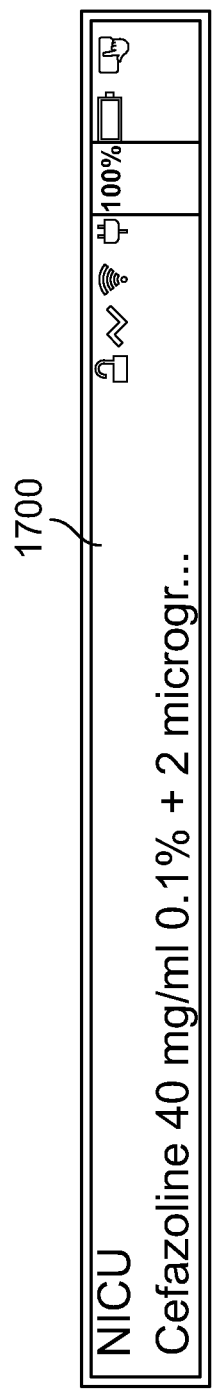
FIGS. 23A-23B are screenshots of displays for a long drug name for an infusion pump touchscreen, according to an embodiment.
Figure 23B:
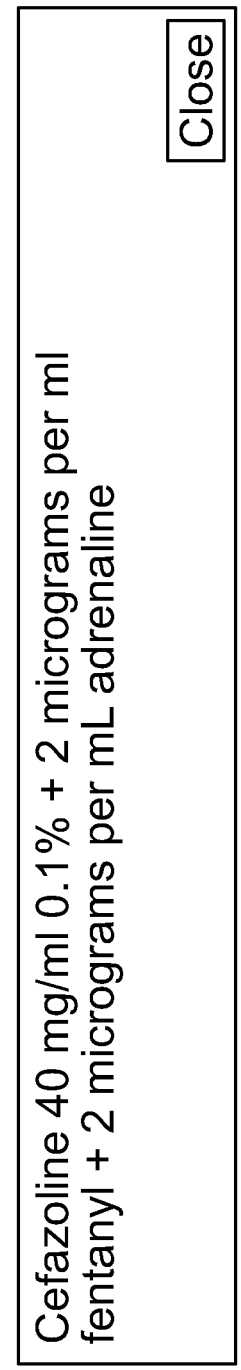

Referring to FIGS. 23A-23B, screenshots of displays for a long name for an infusion pump touchscreen are depicted, according to an embodiment. For example, referring to FIG. 23A, a long name is partially displayed in the title bar, ending with ellipses. The relevant portion of the title bar with the long name further comprises touch target 1700. A user can tap touch target 1700 to present the full drug name in a long name message screen, as illustrated in FIG. 23B. In an embodiment, the long name message screen does not close unless the user closes it. It is important for the user to be able to see the entire drug with as much time as he needs. Accordingly, in an embodiment, the long name message screen does not time out. In an embodiment, when launched or initiated from one of the select protocol screens (See Table 5), the long name message screen has "Select" and "Close" buttons. In an embodiment, when launched from one of the view only screens (See Table 5), the long name message screen has a "Close" button but no "Select" button.

It is to be particularly appreciated and understood that embodiments described by example or otherwise contemplated herein pertaining to user experience for infusion pumps, including syringe pumps and LVPs, are intended to promote intuitive operation of the pumps while also enhancing efficiency and safety in their setup and operation. For example, the various touchscreen presentations, displays, operations, and functions are designed to be intuitive for a user who is interacting with the touchscreens. Such intuitive presentations, displays, operations, and functions are demonstrated by, for example, workflows established among the variously progressive screens such as those shown in, e.g., FIGS. 15-16 regarding drug protocol alphanumeric page lookup and alphanumeric keypad screens. Efficiency and safety in setup and operation of the pumps are therefore enhanced since, for example, a user such as a busy nurse can concentrate on an overall condition of a patient rather than needing to devote extensive focus on and attention to pump setup and operation.

It is also to be particularly appreciated and understood that embodiments described by example or otherwise contemplated herein pertaining to user experience for infusion pumps, including syringe pumps and LVPs, are intended to synergistically and harmoniously work with other "ease of use" features that can be advantageously provided with certain infusion pumps. For example, in some embodiments, all pump components with which a user is intended to interact can be specially color-coded. In an example of a syringe pump, each area of the pump that is physically intended for user interaction or manipulation can be, for example, visually color-coded blue. Accordingly, in a syringe pump, a bumper, a trigger, physical, mechanical actuation buttons such as keypad 106, a barrel clamp lever, a USB port, an Ethernet connector, and a racking/stacking catch and latch button can be colored blue. Similarly, in an LVP, physical, mechanical actuation buttons such as keypad 106, a USB port, an Ethernet connector, and a racking/stacking catch and latch button can be colored blue. The same blue color can also be present in the various touch-screen interaction portions that are designed to be intuitive for a user, so that a cohesive user experience is achieved with regard to these features.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A system for controlling an infusion pump display, the infusion pump including a processor, memory operably coupled to the processor, and display logic comprising instructions that, when executed, cause the processor to:
   display a first subset of infusion parameters on a first running screen of the infusion pump;
   display a second subset of infusion parameters on a second running screen of the infusion pump, wherein the first subset of infusion parameters is greater than the second subset of infusion parameters and the display of the first subset of infusion parameters is in a smaller presentation size than the display of the second subset of infusion parameters;
   evaluate a condition related to the infusion pump; and
   based on the evaluation of the condition and use of a predictive algorithm, automatically and without user intervention, display a specialized screen related to a current status of the system,
   wherein the predictive algorithm is based on previously recorded transitions between screens and data associated with the transitions.

2. The system of claim 1, wherein the specialized screen comprises at least one of data, a programming field, a parameter, or a graph related to the condition.

3. The system of claim 1, wherein the system further comprises a sensor configured to provide a measurement related to the infusion pump, wherein the display logic instructions causing the processor to evaluate the condition related to the infusion pump includes evaluating the measurement, and wherein the specialized screen is based on the measurement.

4. The system of claim 3, wherein the sensor is a flow sensor and the specialized screen comprises a graph of the flow detected by the flow sensor.

5. The system of claim 1, wherein the condition is an alarm condition and the display logic further comprises instructions to, automatically and without user intervention, re-display the first running screen.

6. The system of claim 1, wherein the display logic further comprises instructions to evaluate a second condition related to the infusion pump and based on the evaluation of the second condition, automatically and without user intervention, re-display the second running screen.

7. The system of claim 1, wherein the display logic instructions causing the processor to evaluate the condition related to the infusion pump includes at least one of a predictive algorithm determination, a near-field communication component determination, a peripheral device connection determination, or a signature determination.

8. The system of claim 1, wherein the predictive algorithm is further based on trend lines to determine a most desired or most often entered screen for a particular set of infusion pump or system characteristics.

* * * * *